US012758799B2

(12) United States Patent
Savic et al.

(10) Patent No.: US 12,758,799 B2
(45) Date of Patent: Oct. 13, 2026

(54) WEARABLE ULTRASOUND DEVICE AND HARNESS FOR IMMUNOMODULATION, AND USES THEREOF

(71) Applicant: INIA Biosciences, Inc., Wilmington, DE (US)

(72) Inventors: Dragana Savic, Oxford (GB); Shen Ning, Boston, MA (US)

(73) Assignee: INIA Biosciences, Inc., Wilmington, DE (US)

( * ) Notice: Subject to any disclaimer, the term of this patent is extended or adjusted under 35 U.S.C. 154(b) by 0 days.

(21) Appl. No.: 18/727,470

(22) PCT Filed: Jan. 12, 2023

(86) PCT No.: PCT/US2023/060538
§ 371 (c)(1),
(2) Date: Jul. 9, 2024

(87) PCT Pub. No.: WO2023/137368
PCT Pub. Date: Jul. 20, 2023

(65) Prior Publication Data

US 2025/0073503 A1 Mar. 6, 2025

Related U.S. Application Data

(60) Provisional application No. 63/299,131, filed on Jan. 13, 2022.

(51) Int. Cl.
*A61N 7/00* (2006.01)

(52) U.S. Cl.
CPC ........ *A61N 7/00* (2013.01); *A61N 2007/0026* (2013.01)

(58) Field of Classification Search
None
See application file for complete search history.

(56) References Cited

U.S. PATENT DOCUMENTS 3,525,330 A 8/1970 Reginald et al.
5,762,616 A 6/1998 Talish
(Continued)

FOREIGN PATENT DOCUMENTS

EP 2042093 A1 4/2009
KR 20210016346 A 2/2021
(Continued)

OTHER PUBLICATIONS

Borovikova, L.V. et al. (May 25, 2000). "Vagus Nerve Stimulation Attenuates The Systemic Inflammatory Response To Endotoxin," Nature 405:458-462.
(Continued)

*Primary Examiner* — Jonathan Cwern
(74) *Attorney, Agent, or Firm* — Morrison & Foerster LLP

(57) ABSTRACT

Provided herein are wearable harnesses for securing and positioning an ultrasound device on a subject. The wearable harnesses can be used to position an ultrasound transducer to a human body. The wearable harnesses may include two adjustable shoulder straps, an adjustable waist strap, a pocket for holding a power pack, and a pocket for holding the transducer. For example, the pocket for holding the transducer may be positioned over the subject's spleen such that the ultrasound transducer may be positioned over the subject's spleen. Provided herein is also a treatment unit to be used to the wearable harness, that includes an ultrasound transducer; and a mechanical lens comprising a plurality of concentric rings and configured to adjust ultrasonic waves emitted by the ultrasound transducer.

14 Claims, 27 Drawing Sheets

(56) References Cited

U.S. PATENT DOCUMENTS

| | | | | |
|---|---|---|---|---|
| 6,126,608 | A | 10/2000 | Kemme | |
| 6,834,206 | B1 | 12/2004 | Pitzen | |
| 8,585,597 | B2 | 11/2013 | Dae | |
| 8,763,562 | B2 | 7/2014 | Fladl | |
| 9,511,228 | B2 | 12/2016 | Amurthur | |
| 10,667,795 | B2 | 6/2020 | Ensenaliev | |
| 10,702,243 | B2 | 7/2020 | Yang | |
| 11,064,924 | B2 | 7/2021 | Woltjer | |
| 11,090,688 | B2 | 8/2021 | Bhardwaj | |
| 11,149,243 | B2 | 10/2021 | Jeon | |
| 11,207,051 | B2 | 12/2021 | Beckers | |
| 11,213,275 | B2 | 1/2022 | Hakkens | |
| 2002/0091339 | A1* | 7/2002 | Horzewski | A61N 7/00 601/2 |
| 2005/0107842 | A1 | 5/2005 | Rezai | |
| 2005/0228459 | A1 | 10/2005 | Levin | |
| 2006/0212076 | A1 | 9/2006 | Demarais | |
| 2006/0212078 | A1 | 9/2006 | Demarais | |
| 2011/0208095 | A1 | 8/2011 | Jolesz | |
| 2012/0065501 | A1 | 3/2012 | Dae | |
| 2012/0135392 | A1 | 5/2012 | El-bialy | |
| 2012/0209118 | A1* | 8/2012 | Warnking | A61B 8/085 601/2 |
| 2016/0038753 | A1 | 2/2016 | Chornenky | |
| 2016/0038770 | A1 | 2/2016 | Tyler | |
| 2017/0007853 | A1 | 1/2017 | Alford | |
| 2017/0100589 | A1 | 4/2017 | Schwab | |
| 2018/0028841 | A1 | 2/2018 | Konofagou | |
| 2018/0126418 | A1 | 5/2018 | Bhardwaj | |
| 2019/0247678 | A1 | 8/2019 | Konofagou | |
| 2019/0282164 | A1 | 9/2019 | Saroka | |
| 2019/0321640 | A1 | 10/2019 | Carmena | |
| 2020/0054228 | A1 | 2/2020 | Puleo | |
| 2020/0188696 | A1* | 6/2020 | Rousso | A61N 7/00 |
| 2021/0187330 | A1 | 6/2021 | Bailey | |
| 2021/0361977 | A1 | 11/2021 | Jordan et al. | |
| 2022/0080197 | A1 | 3/2022 | Lim | |

FOREIGN PATENT DOCUMENTS

| | | | |
|---|---|---|---|
| WO | 2010022239 | A2 | 2/2010 |
| WO | 2017192754 | A1 | 11/2017 |
| WO | 2018022902 | A1 | 2/2018 |
| WO | 2020185734 | A1 | 9/2020 |
| WO | 2021188200 | A2 | 9/2021 |
| WO | 2021222892 | A1 | 11/2021 |
| WO | 2022011327 | A1 | 1/2022 |
| WO | 2023137368 | A1 | 7/2023 |

OTHER PUBLICATIONS

Bryant, D. et al. (Apr. 14, 1998). "Cardiac Failure In Transgenic Mice With Myocardial Expression Of Tumor Necrosis Factor-α," Circulation 97:1375-1381.

Cotero, V. et al. (2019, e-pub. Mar. 12, 2019). "Noninvasive Sub-Organ Ultrasound Stimulation For Targeted Neuromodulation," Nature Communications 10(952):1-12.

De Jonge, W.J. et al. (2007, e-pub. May 14, 2007). "The Alpha7 Nicotinic Acetylcholine Receptor As A Pharmacological Target For Inflammation," British Journal of Pharmacology 151:915-929.

Deng, J. et al. (Sep. 2004, e-pub. May 19, 2004). "Adrenergic Modulation Of Splenic Macrophage Cytokine Release In Polymicrobial Sepsis," American Journal of Physiology-Cell Physiology 287:C730-C736.

Dinarello, C.A. (Jun. 1991). "The Proinflammatory Cytokines Interleukin-1 And Tumor Necrosis Factor And Treatment Of The Septic Shock Syndrome," Journal of Infectious Diseases 163(6):1177-1184.

Donegà, M. et al. (May 10, 2021). "Human-Relevant Near-Organ Neuromodulation Of The Immune System Via The Splenic Nerve," PNAS 118(20):e2025428118, 1-12.

Downs, M.E. et al. (2018). "Non-Invasive Peripheral Nerve Stimulation Via Focused Ultrasound In Vivo," Phys. Med. Biol. 63(035011):27 pages.

Ferreira, V.L. et al. (2018). "Cytokines And Interferons: Types And Functions," Chapter 4 in Autoantibodies and Cytokines, Khan, W.A. ed., Intechopen: London, UK, pp. 65-87.

Gigliotti, J.C. et al. (2013). "Ultrasound Prevents Renal Ischemia-Reperfusion Injury By Stimulating The Splenic Cholinergic Anti-Inflammatory Pathway," J Am Soc Nephrol 24(9):1451-1460, 11 pages.

Gigliotti, J.C. et al. (2015). "Ultrasound Modulates The Splenic Neuroimmune Axis In Attenuating AKI," J Am Soc Nephrol 26(10):1-12.

Graham, R.S. et al. (2020). "First-In-Human Demonstration Of Splenic Ultrasound Stimulation For Non-Invasively Controlling Inflammation," medRxiv, 30 pages.

Hricik, D.E. et al. (2003). "Enzyme Linked Immunosorbent Spot (ELISPOT) Assay For Interferon-Gamma Independently Predicts Renal Function In Kidney Transplant Recipients," American Journal of Transplantation 3:878-884.

Huerta, T.S. et al. (2021, e-pub Mar. 3, 2021). "Targeted Peripheral Focused Ultrasound Stimulation Attenuates Obesity-Induced Metabolic And Inflammatory Dysfunctions," Scientific Reports 11(5083):1-12.

Huston, J.M. et al. (Jul. 10, 2006). "Splenectomy Inactivates The Cholinergic Anti-Inflammatory Pathway During Lethal Endotoxemia And Polymicrobial Sepsis," J Exp Med 203(7):1623-1628.

International Search Report and Written Opinion from the International Searching Authority mailed May 3, 2023, for International Patent Application No. PCT/US2023/060538 filed on Jan. 12, 2023, 12 pages.

Kalkman, H.O. et al. (2016, e-pub. Mar. 15, 2016). "Modulatory Effects Of α7 nAChRs On The Immune System And Its Relevance For CNS Disorders," Cel. Mol. Life Sci. 73(13):2511-2530.

Kefauver, J.M. et al. (Nov. 2020). "Discoveries In Structure And Physiology Of Mechanically Activated Ion Channels," Nature 587(7835):567-576, 26 pages.

Koopman, F.A. et al. (Jul. 19, 2016). Vagus Nerve Stimulation Inhibits Cytokine Production And Attenuates Disease Severity In Rheumatoid Arthritis PNAS 113(29):8284-8289.

Kubanek, J. et al. (Apr. 26, 2016). "Ultrasound Modulates Ion Channel Currents," Scientific Reports 6(24170):1-14.

Li, S. et al. (2021, e-pub. Mar. 29, 2021). "Vagus Nerve Stimulation Enhances The Cholinergic Anti-Inflammatory Pathway To Reduce Lung Injury In Acute Respiratory Distress Syndrome Via STAT3," Cell Death Discovery 7(63):1-9.

Lin, Z. et al. (May 22, 2019). "Ultrasound Stimulation Modulates Voltage-Gated Potassium Currents Associated With Action Potential Shape In Hippocampal CA1 Pyramidal Neurons," Frontiers in Pharmacology 10(544):1-11.

Mina-Osorio, P. et al. (2012, e-pub. Feb. 14, 2012). "Neural Signaling In The Spleen Controls B-Cell Responses To Blood-Borne Antigen," Molecular Medicine 18:618-627.

Mori, D.N. et al. (Mar. 2014). "Inflammatory Triggers Of Acute Rejection Of Organ Allografts," Immunological Reviews 258(1):132-144, 19 pages.

Nizri, E. et al. (2009). "Activation Of The Cholinergic Anti-Inflammatory System By Nicotine Attenuates Neuroinflammation Via Suppression Of Th1 And Th17 Responses," The Journal of Immunology 183:6681-6688.

Piotti, G. et al. (Oct. 2014, e-pub. Oct. 21, 2014). "Vascular Endothelium As A Target Of Immune Response In Renal Transplant Rejection," Frontiers in Immunology 5(505):1-9.

Platanias, L.C. (May 2005). "Mechanisms Of Type-I-And Type-II-Interferon-Mediated Signalling," Nature Reviews Immunology 5(5):375-386.

Rosas-Ballina, M. et al. (Aug. 5, 2008). "Splenic Nerve Is Required For Cholinergic Antiinflammatory Pathway Control Of TNF In Endotoxemia," PNAS 105(31):11008-11013.

Rosin, D.L. et al. (2011). "Dangers Within: DAMP Responses To Damage And Cell Death In Kidney Disease," J Am Soc Nephrol 22(3):416-425.

(56) References Cited

OTHER PUBLICATIONS

Serteser, M. et al. (Oct. 2002, e-pub. Aug. 29, 2002). "Changes In Hepatic TNF-α Levels, Antioxidant Status, And Oxidation Products After Renal Ischemia/Reperfusion Injury In Mice," Journal of Surgical Research 107:234-240.
Siegmund, B. et al. (1998). "Adrenaline Enhances LPS-Induced IL-10 Synthesis: Evidence For Protein Kinase A-Mediated Pathway," International Journal of Immunopharmacology 20:57-69.
Tracey, K.J. (Feb. 2007). "Physiology And Immunology Of The Cholinergic Antiinflammatory Pathway," The Journal of Clinical Investigation 117(2):289-296.
Zachs, D.P. et al. (2019, Mar. 12, 2019). "Noninvasive Ultrasound Stimulation Of The Spleen To Treat Inflammatory Arthritis," Nature Communications 10(951):1-10.
Zhang, A. et al. (Mar. 2021, e-pub. Dec. 3, 2020). "Pulsed Ultrasound Of The Spleen Prolongs Survival Of Rats With Severe Intra-Abdominal Sepsis," Journal of Surgical Research 259:97-105.

* cited by examiner

Without Lens

With 20 mm Focal Distance Lens

WEARABLE ULTRASOUND DEVICE AND HARNESS FOR IMMUNOMODULATION, AND USES THEREOF

CROSS-REFERENCE TO RELATED APPLICATIONS

This application is a U.S. national stage application under 35 U.S.C. § 371 of International Application No. PCT/US2023/060538, filed internationally on Jan. 12, 2023, which claims priority to and benefit of U.S. Provisional Patent Application No. 63/299,131 filed Jan. 13, 2022.

FIELD

The present disclosure relates generally to wearable harnesses, and, more specifically, wearable harnesses for securing and positioning an ultrasound device on a subject.

BACKGROUND

The nervous system is the major system that controls, regulates, and communicates between the body and the brain. Bioelectronic medicine is based on the idea that stimulating a nerve can affect biological functions. More and more medical devices applied to nerves are emerging as treatment for diseases, from regulating blood glucose levels to curbing pain, and even treating inflammatory disease such as rheumatoid arthritis, etc. Bioelectronic biomedicine technologies include anything from electrical signal to electromagnetic fields to even ultrasound, and there has been development of both invasive implantable devices that are wrapped around a nerve or non-invasive stimulation such as cochlear and nerve stimulation at the surface of the skin. More recently, Cotero et al. showed that suborgan non-invasive low-intensity ultrasound can alleviate cytokine production and even hyperglycemia in a model of endotoxin-induced hyperglycemia and cytokine production. Furthermore, Huerta et al. showed that focused ultrasound can alleviate liver inflammation and reduce fat accumulation in an obese pre-clinical model. The results were comparable with traditionally invasive vagus nerve stimulation (VNS) devices that have been shown to induce a similar response, suggesting the possibility that a non-invasive approach via ultrasound can have a similar clinical effect as the more invasive approaching of directly stimulating the relevant nerve via implantable electrodes or cuffs.

Development of invasive electrical stimulation devices to treat chronic diseases is ongoing.

With respect to inflammatory diseases, the cholinergic anti-inflammatory pathway is known to modulate the mammalian immune response. The parasympathetic vagus nerve can transmit signals from the brain to the adrenergic splenic nerve, which interacts with splenic immune cells to modulate the immune system. The splanchnic sympathetic nerves synapse at the celiac-superior mesenteric plexus ganglion with the splenic nerve. Specifically, stimulation of the splenic nerve releases norepinephrine which stimulates splenic T cells that can then subsequently signal to the cytokine producing macrophages to reduce pro-inflammatory cytokine production. VNS has been shown to reduce production of cytokines like TNF-$\alpha$ and other interleukines associated with inflammatory diseases like rheumatoid arthritis, Crohn's disease, chronic kidney disease, and psoriasis. Furthermore, ultrasound stimulation has shown to be able to induce similar electrical activity for treatment of peripheral neuropathic disease in the clinic.

With respect to kidney/organ rejection/organ transplant, every 10 minutes, a patient (e.g., human or subject) is added to the national kidney transplant waiting list. In 2019, 91,834 kidneys were transplanted worldwide, costing $40.6B. In 2018, 20,000 kidneys were transplanted in the USA, meeting 20% of the US demand alone. Kidney transplantation is the only curative treatment for patients with end-stage renal disease who have a 70% 5-year mortality on dialysis. End-stage renal disease patients often require dialysis three times a week at a medical center, considerably reducing their quality of life. Global Burden of Disease study attributes 2.17% of deaths every year and 1.47% of disability-adjusted life years (DALYs) to chronic kidney disease. Unfortunately, up to 30% of people who receive a kidney transplant experience some degree of rejection, and this number has not been significantly changed in the past 40 years. Most rejections occur within six months after transplantation but can occur at any time, even years later. Prompt treatment can reverse the rejection in most cases and prevent further organ damage, but current treatments are mostly anti-inflammatory drugs and immunosuppressant drugs that have undesirable side effects, are hard to personalize, and are not ideal for long-term use.

In addition, there are studies showing that kidney transplant patients have elevated cytokine levels related to a systemic inflammatory response to the foreign organ, and that this is an underlying cause of kidney rejection.

Noninvasive ultrasound (US) stimulation targeting the spleen has been explored as a safe and effective alternative to invasive or systemic anti-inflammatory treatment. US stimulation targets the cholinergic anti-inflammatory pathway consisting of the vagus nerve to spleen circuit. This treatment was shown to have protective and therapeutic effects a K/B×N serum-transferred model of inflammatory arthritis, a rheumatoid arthritis (RA) mouse model, both when it was applied before or at the beginning of the disease. Single-cell RNA sequencing revealed that in T and B-cells, certain genes are upregulated in arthritis mice after receiving US treatment. Those genes included transcription factors c-Jun and JunB. C-Jun and JunB can form dimers, thus forming the transcription factor AP-1, which induces the transcription of pro-inflammatory genes. Further, both B and T-cells increased the transcription of genes involved in microtubule formation (like Ssh2) and crosslinking upon US treatment. This suggests that alterations in the cytoskeleton could alter the polarization or migration of lymphocytes, so that immune cell infiltration and inflammation are reduced. This is supported by the finding that upon vagus nerve stimulation, B cells showed reduced antibody production migration, which led them to aggregate in the marginal zone of the spleen. This demonstrates that the anti-inflammatory pathway regulates immune cell migration. Further, splenic US treatment of rats with intra-abdominal sepsis decreased TNF-a and MCP-1 levels.

In mice exposed to US before renal ischemia, the treatment protected kidney function and morphology, mediated by CD4+ T-cells. T-cell dependency of this effect was confirmed by using both an $\alpha$7nAChR agonist and antagonist as well as $\alpha$7nAChR deficient mice, which did not show the protective effect. This study identified the cholinergic anti-inflammatory pathway as an essential mediator of the anti-inflammatory effect of ultrasound, possibly by interacting with the splenic nerve, as it was previously shown to be the case in sepsis. The isolation and transfer of splenocytes from ultrasound treated mice into naïve mice alone had a protective effect on the kidney during IRI and CLP-induced sepsis, suggesting that ultrasound treatment may have changed the phenotype of these cells. Further, it has been demonstrated that this effect depends on the splenic nerve, as the deleterious effect of a splenectomy was also achieved by splenic denervation alone. This supports the findings that suggest that the spleen is involved in modulating inflammation during kidney injury mediated by the splenic nerve.

The α7 nicotinic acetylcholine receptor belongs to a family of ion channel receptors. Various types of immune cells, like B-cells, T-cells, microglia, monocytes and macrophages or dendritic cells, express the α7 nicotinic acetylcholine receptor and therefore respond to nicotine. Acetylcholine binding to α7nAChR triggers $Ca^{2+}$ and sodium influx, which leads to neurotransmitter release in neuronal cells. In non-neuronal cells, $Ca^{2+}$ influx causes calcium to be released from stores. In addition, kinases and phosphatases are activated, which results in signaling cascades that are independent from ion flux. For example, α7nAChR activation can inhibit TLR3/4/9 signaling, which promote the secretion of pro-inflammatory cytokines. In macrophages, the receptor can recruit Jak2, which induces the phosphorylation and activation of STAT3. This pathway is associated with the production of anti-inflammatory mediators. Downstream, it prevents the activation of the pro-inflammatory NF-kB pathway, which triggers pro-inflammatory cytokine production. Further, p38 MAP-kinase activation is inhibited, which prevents the release of pro-inflammatory cytokines like TNFa. In T-cells, it was suggested that the expression of α7nAChR is up-regulated during immune activation. Treatment with nicotine was shown to reduce T cell proliferation and the release of pro-inflammatory Th1 (TNF, IFN-y) and Th17 (IL-17, IL-17FIL-21, IL-22) cytokines, while anti-inflammatory IL-4 levels were increased. The activation of the receptor promoted a shift from Th1 to Th2 cells. NF-kB activation and IL-2 production were reduced after treatment. These effects were sufficient to reduce experimental autoimmune encephalomyelitis severity as well as immune cell infiltration and demyelination.

Further, US treatment inhibited the recruitment of neutrophils and myeloid cells into the kidney during renal ischemia. Macrophages play a key role in inflammation by producing cytokines. Therefore, modulating their activity may be a promising approach to treat or prevent inflammation in acute kidney rejection (AKI). Adrenergic stimulation was shown to inhibit the secretion of pro-inflammatory cytokines like TNF-a or IL-6 by splenic macrophages in a sepsis mouse model through an up-regulation of IL-10. This process is thought to be mediated by protein kinase A. The same effect was observed in an endotoxemia model, where vagus nerve stimulation reduced TNF production by macrophages in the spleen, while α7 KO abolished this effect. Modulation of splenic macrophage behavior in inflammation depends on the cholinergic anti-inflammatory pathway specifically through a preganglionic, which originates in the dorsal motor nucleus of the vagus nerve, and a second postganglionic, originating in the celiac-superior mesenteric plexus, and projecting in the splenic nerve. Interestingly, the immunomodulary properties of splenic nerve stimulation seem to be translatable to other animal models and even humans. A study using pigs as a model for human splenic innervation demonstrated that splenic nerve stimulation protects the animals from cardiovascular damage and reduces cytokine production upon LPS exposure. In a rodent endotoxemia model, pro-inflammatory cytokines TNF, IL-6, IFN-y, IL-1β, IL-1a and IL-12 were reduced in splenic lysates after splenic ultrasound. A first study compared the effects of US treatment on healthy individuals and five RA patients. US treatment of the spleen of healthy individuals for only three minutes was sufficient to reduce TNF production in the blood when it was exposed to LPS ex vivo. Daily splenic US treatment of RA patients resulted in the reduction of mRNA levels of pro-inflammatory cytokines such as IL-1β and IL-8 by monocytes. In CD8+ T-cells, IFN-y transcription was inhibited. Apart from cytokine expression, cytokine receptors like those for TNF, IL-6, IL-17, IL-13 and IFN-y, were also down-regulated in monocytes. Further, pro-inflammatory pathways resulting in IL-6 or TNF production, like the NF-kB pathway, were inhibited. Pathways promoting monocyte migration were also down-regulated, while the adaptive immune response and the circulating immune cell composition remained unchanged. This suggests that the treatment is safe and does not induce overall immune suppression. Intriguingly, splenic US is also tested as a COVID-19 treatment to decrease inflammation and reduce the length of hospitalization. A pilot clinical trial is set out to determine whether the US has a beneficial effect in severe COVID-19 infections (Trial number: NCT04803409). This may be a promising approach considering vagus nerve stimulation in an acute respiratory distress syndrome (ARDS) model decreased CXCL9 mRNA levels and the secretion of pro-inflammatory cytokines TNF-a and IL-1β while increasing IL-10 levels. Further, the treatment seemed to switch macrophage polarization from a pro-inflammatory M1 to an anti-inflammatory M2 phenotype.

Conventional ultrasound systems comprise multiple components, including—but not limited to—a transducer to direct ultrasonic waves into a subject's body, a handle or wand attached to the transducer, and a display screen. These ultrasound systems require a medical professional to operate and may utilize a conductive gel to fill air gaps between the transducer and the subject's body. In conventional ultrasound systems, the medical professional first applies the conductive gel to the subject's body, then holds the transducer in contact with the subject's body by continuously applying pressure through the handle or wand. The images produced are displayed in real time on the display screen. In order to position the transducer accurately, the medical professional moves the transducer across the subject's body until a target feature appears on the display screen. External measurement tools may sometimes be necessary to position the transducer accurately on the subject's body.

BRIEF SUMMARY

In some aspects, provided are wearable harnesses for securing and positioning an ultrasound transducer on a subject's body. The wearable harnesses provided herein can include two adjustable shoulder straps, an adjustable waist strap, a pocket for holding a power pack, and a securing portion for holding the transducer. In some embodiments, the pocket for holding the transducer is positioned over the subject's spleen.

The conventional ultrasound systems described above are typically used for medical imaging. In recent years, some ultrasound systems have additionally been modified for immunomodulation. During immunomodulation, the ultrasonic waves emitted by these ultrasound systems stimulate nerves, such as the splenic nerve, into modulating the immune system. Ultrasound immunomodulation may be desirable over other immunomodulation treatments because it is non-invasive and does not require drugs to modulate immune pathways.

Like conventional imaging ultrasound systems, the transducers of immunomodulatory ultrasound systems are typically positioned and operated by a medical professional during treatment. However, many subjects may desire to undergo at-home ultrasound treatment without requiring the presence of a medical professional for every treatment.

Accordingly, in certain aspects, the harnesses (e.g., garment or back brace) provided herein allow a subject to consistently position and operate the transducer over a target organ or nerve, such as the splenic nerve, without requiring the presence of a medical professional. Unlike the conventional handheld transducers described above, the transducers described herein are attached to a wearable harness that is fastened to a subject's body. The transducer is placed on the wearable harness with a securing portion/mechanism and positioned over the subject spleen, which contains the splenic nerve, by a medical professional. A separate pocket of the wearable harness holds a power pack for the transducer. Additionally, the wearable harness includes adjustable shoulder and waist straps so that a medical professional can adjust the harness to fit the subject's body and secure the transducer over the subject's spleen. In some embodiments, the harnesses described herein may be configured to position an ultrasonic transducer over a liver (sympathetic fibers from the celiac plexus and parasympathetic fibers from the anterior and posterior vagal trunks) or another organ or nerve. In some embodiments, a positioning grid may be provided on the adjustable straps and/or the transducer securing portion to assist in the positioning of the transducer. Once the straps are adjusted, the transducer will be positioned in the same location above the subject's spleen every time the harness is worn. Thus, the subject can wear, activate, and remove the harness without requiring a medical professional to readjust the harness before every ultrasound treatment. This enables the subject to receive at-home ultrasound treatment without the presence of a medical professional.

In some embodiments, the wearable harness may be in the form of a belt, vest, or patch, that allows for consistent stimulation of the target organ.

In some embodiments, the wearable harness stimulates the splenic nerve (by directly targeting the spleen) to reduce inflammatory markers in the body such as, but not limited to, TNF-alpha, IL6.

The wearable harness may be configured and used to stimulate any other nerve or organ to modulate physiological function. Advantageously, no medical professional is needed, and the ultrasound device can be worn directly on the skin, while the user goes about their normal daily activities.

In some embodiments, provided is a system for securing an ultrasound transducer over a spleen of a subject, the system comprising: a harness comprising: a front portion configured to hold a power pack; a rear portion connected to the front portion by a first shoulder strap and a second shoulder strap; an adjustable waist strap configured to wrap around a subject's waist and connect the front portion and the rear portion; and a transducer securing portion located on the adjustable waist strap and configured to be positioned over a spleen of a subject, wherein the transducer securing portion comprises a two-dimensional scale; and a treatment unit comprising: an ultrasound transducer configured to couple to the transducer securing portion of the harness; and a mechanical lens positioned between the ultrasound transducer and the subject, the mechanical lens comprising a plurality of concentric rings and configured to adjust ultrasonic waves emitted by the ultrasound transducer.

In some embodiments, provided a harness for positioning an ultrasound transducer to a subject, the harness comprising: a front portion configured to hold a power pack; a rear portion connected to the front portion by a first shoulder strap and a second shoulder strap; an adjustable waist strap configured to wrap around a subject's waist and connect the front portion and the rear portion; and a transducer securing portion located on the adjustable waist strap and configured to be positioned over a spleen of a subject, wherein the transducer securing portion comprises a two-dimensional scale.

In some embodiments, provided is a treatment unit comprising: an ultrasound transducer; and a mechanical lens comprising a plurality of concentric rings and configured to adjust ultrasonic waves emitted by the ultrasound transducer.

In some embodiments, provided is a system for securing an ultrasound transducer over a spleen of a subject, the system comprising: a harness comprising: a front portion configured to hold a power pack; a rear portion connected to the front portion by a first shoulder strap and a second shoulder strap; an adjustable waist strap configured to wrap around a subject's waist and connect the front portion and the rear portion; and a transducer securing portion located on the adjustable waist strap and configured to be positioned over a spleen of a subject, wherein the transducer securing portion comprises a two-dimensional scale, and an ultrasound transducer configured to couple to the transducer securing portion of the harness.

In some embodiments, provided is a harness for positioning an ultrasound transducer to a subject, the harness comprising: a transducer securing portion configured to receive an ultrasound transducer and secure the ultrasound transducer in a first location directly over a spleen of a subject.

In some embodiments, provided is a method of using a harness for positioning an ultrasound transducer to a subject, the method comprising: securing a treatment unit to a transducer securing portion of a harness; placing the harness on a subject such that the treatment unit is positioned over a spleen of the subject.

BRIEF DESCRIPTION OF THE DRAWINGS

The invention will now be described, by way of example only, with reference to the accompanying drawings, in which.

DETAILED DESCRIPTION

Figure 1:
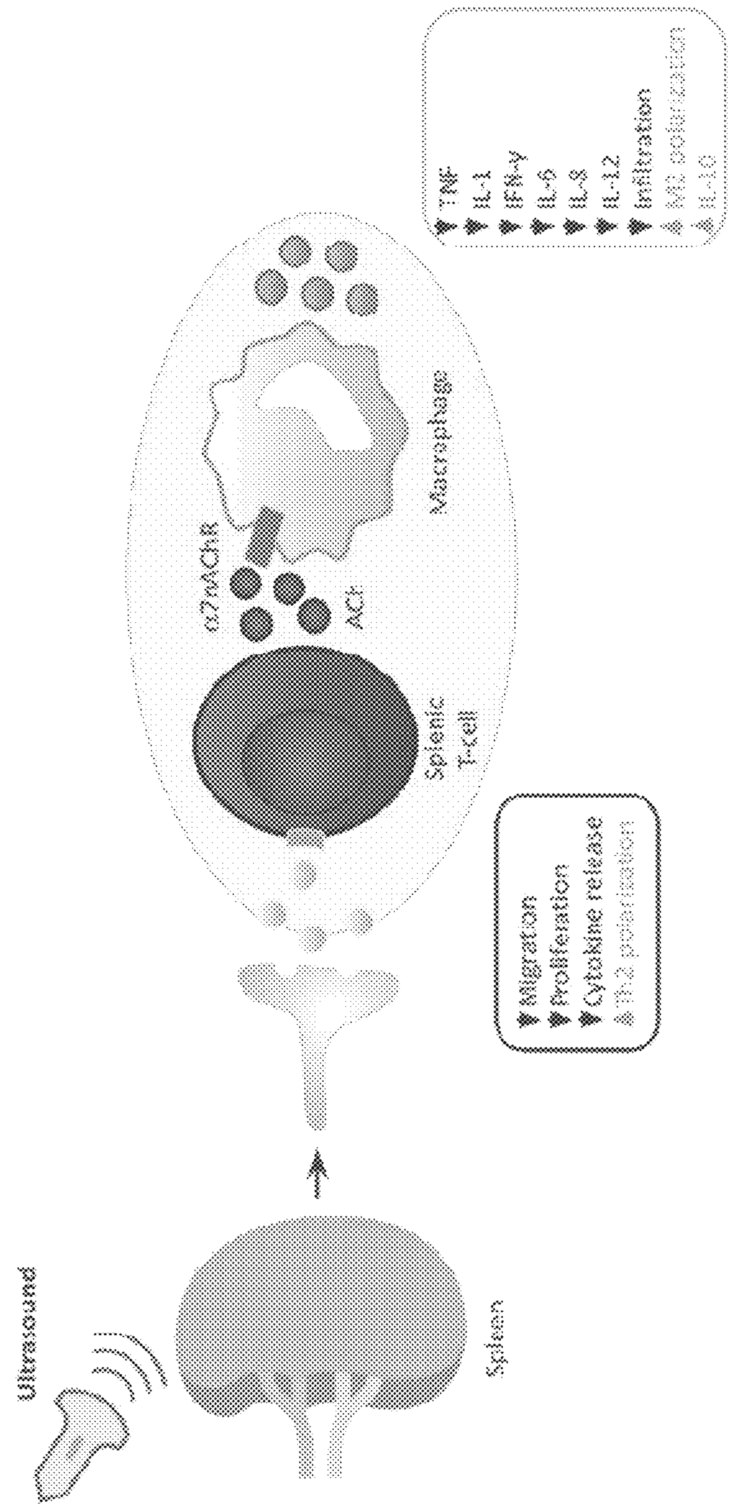
FIG. 1 is a diagram illustrating the scientific rationale for the mechanism of action, according to some embodiments.

In some aspects, provided are wearable harnesses positioning an ultrasound transducer to a subject's body. The wearable harnesses provided herein can include two adjustable shoulder straps, an adjustable waist strap, a pocket for holding a power pack, and a securing portion for holding the transducer. In some embodiments, the pocket for holding the transducer is positioned over the subject's spleen such that the ultrasound transducer may be positioned over the subject's spleen.

As explained above, conventional ultrasound systems are typically used for medical imaging. In recent years, some ultrasound systems are being used for immunomodulation. During immunomodulation, the ultrasonic waves emitted by these ultrasound systems stimulate nerves, such as the splenic nerve, into modulating the immune system in a non-invasive manner. Like conventional imaging ultrasound systems, the transducers of immunomodulatory ultrasound systems are typically positioned and operated by a medical professional during treatment.

Conversely, the harnesses provided herein allow a subject to consistently position and operate the transducer over a target, such as the splenic nerve, without requiring the presence of a medical professional. The transducers described herein are attached to a wearable harness that is fastened to a subject's body. The transducer is placed at a securing portion of the wearable harness that is configured to be positioned over the subject's spleen during proper fit and wear. When properly fit (e.g., adjusted) to the subject, the transducer can be positioned in the same location every time the harness is worn. Thus, the subject can wear, activate, and remove the harness without requiring a medical professional to readjust the harness before every ultrasound treatment. This enables the subject to receive at-home ultrasound treatment without the presence of a medical professional. In some embodiments, a harness can include commercially available and smart materials that can adapt to the body's shape, retain memory of the body, and ensure security of the ultrasound stimulator to provide continue ultrasound to a specific region of the target organ.

The wearable harnesses described herein can also be used to treat subjects shortly after an organ transplant. Unfortunately, only 20% of organ demand in the world is met. Even if a subject receives an organ transplant, one out of three subjects will reject their new organ. The current clinical standard is to put subjects on cocktails of immunosuppressant drugs, that have dangerous side-effects. No major advancements for the management of organ rejection have been seen for the past 40 years. Therefore, more personalized treatment is critical for the survival of these subjects.

Aspects and embodiments of the present invention can suppress the immune system via ultrasound stimulation of a target organ, such as the spleen, in a wearable device that the subject can use at home. Though the clinical effects are similar to the immune suppression observed with drugs, the typical dangerous side-effects are reduced as the system leverages the normal physiology of an individual which contains feedback mechanisms to prevent oversuppression. According to certain embodiments, by targeting the spleen and/or the splenic nerve, normal physiology can be controlled by inhibiting or enhancing its normal function. However, because the approach augments normal physiology, there is no risk for over-suppression as the body's normal feedback loop will be activated to prevent this side effect. According to certain aspects, the innovative design makes it possible for subjects to wear the device like a vest, without any knowledge of anatomy. As discussed in more detail below, according to certain examples, the device is configured to stimulate the spleen, the liver and nerves surrounding it with specific frequency or frequencies that have the desired effects. The wearable harness is fitted once at the clinic, and thereafter it can be modulated by the physician remotely with several parameters such as intensity, frequency, duration and more, depending on the subject response based on biomarker feedback that is taken periodically, e.g., once daily to once weekly, all personalized to the subject.

In some embodiments, the wearable harnesses described herein may, along with an ultrasound transducer, use low or high intensity focused ultrasound (LIFU/HIFU) to treat subjects with organ (e.g., kidney) transplants to prevent chronic or acute organ (e.g., kidney) rejection.

Embodiments of the wearable device are not limited to a wearable back brace, vest, or harness, but also include a patch design as well as a belt. Those skilled in the art, given the benefit of this disclosure, will appreciate that other wearable forms of the device may also be implemented. Regardless of the form or design of the wearable device, the device is configured such that it is fitted and rigid, so that it does not move during treatment.

Furthermore, embodiments of the wearable services and system disclosed herein allow clinics or hospitals to obtain monitored data from subjects. Any data collected during the wearable period may be collected. In some embodiments, the system may be used by subjects who suffer from acute or chronic organ (e.g., kidney) rejection; however, the system and methods of use disclosed herein can be applied to any other indication, not limited to kidney rejection. Embodiments may be used to treat any modulatory marker or any other biological function with the wearable device that can apply ultrasound stimulation to the body without any prior knowledge from the subject or person using it.

Embodiments of the device may be personalized to every single organ and subject. Embodiments of the device may replace all the immunosuppressant drugs, thus being able to deliver a personalized and home-based treatment approach that even has the potential to make studies into artificial kidney obsolete. Examples of advantages and value provided by embodiments of the device include the ability to provide opportunity to 1) reduce the cost of care (through fewer visits and early detection), 2) improve access to care (through home monitoring), and 3) improve outcomes (early detection and specific treatment means less organs wasted and therefore shorter organ transplant waiting list). Furthermore, the collection of data and the use of an artificial intelligence (AI) based cloud platform may allow for optimized and personalized care.

Unlike immunosuppressive drugs, where only the dosage can be adjusted, this technology has many parameters that can be personalized to the subject's need such as: location of stimulation, amplitude, pressure, and frequency of the stimulation, which can even be adjusted in real-time based on the monitored biomarkers. Furthermore, neuromodulation of the immune system via ultrasound stimulation of the splenic nerve may, over time, train the body to maintain a non-inflammatory state whereby the subject requires less immunosuppression via drugs or neuromodulation.

According to certain embodiments, the device can be compiled with companion monitoring devices as well as with artificial intelligence (through software algorithm, machine learning and/or other data processing methods) to predict and optimize the treatment regime. For example, embodiments of the wearable device described herein may include a communicator with a monitoring device (e.g., similar to a glucose monitor) to analyze the effect of the ultrasound stimulation, and either directly or through a cloud-based platform to provide optimization parameters to improve the stimulation.

A device according to certain embodiments is a closed-loop system that integrates biomarker monitoring with an ultrasound stimulator to evoke anti-inflammatory effects. Embodiments of the ultrasound stimulation device, packaged in the form of a wearable device, such as a belt, a patch or a back brace, for example. This technology is designed for the subject to bring home, which allows for the physician to treat subjects at home and adjust treatments remotely. Ultimately by treating subjects via bioelectronics, fewer organs will be fully rejected because they will be managed by the technology according to aspects and embodiments disclosed herein, and thereby resulting in a shorter organ waiting list. Bioelectronic medicine devices leverage the physiological mechanism, and thereby this treatment can never lead to a full suppression of the immune system unlike drugs, this therefore means that these subjects can taper off some of the immunosuppressant drugs with the most dangerous side effects, improving their quality of life significantly.

Immunomodulation Mechanisms

Data has shown that short periods of ultrasound stimulation of the spleen, vagus nerve, or the liver can reduce inflammatory cytokine markers in animal models and in humans. For example, one study shows that ultrasound stimulation of the spleen can be used to treat inflammatory arthritis in mouse models. Another study shows that ultrasound stimulation of the spleen reduces cytokine levels to the same levels as the more medically established procedure, implant-based vagus nerve stimulation. A third study shows that focused ultrasound on the porta hepatis can reduce cytokine markers in obese animals and reduce weight. A final study shows that ultrasound stimulation of the spleen lowers cytokines levels in humans.

Graft Rejection Mechanism: During allograft rejection, host immune cells, mostly T-cells and particularly CD4+ T-cells, recognize polymorphisms within the MHC and the minor histocompatibility complex. The T-cells can either be activated through direct allorecognition by recognizing intact donor MHC molecules on donor-derived APCs or they can be activated via indirect allorecognition by responding to processed donor-derived peptides bound to MHC molecules. Donor endothelial cells can also directly activate CD8+ T-cells, which can be a process constantly present after transplantation[26]. Embodiments of the wearable device according to aspects of the invention have been developed for the novice subject without any prior knowledge of the organs of interest. Therefore, only by placing the back brace, the patch or the belt, the device is fitted in such a way that it can modulate the above processes through targeting nerves connected to the spleen and the liver. Therefore, embodiments of the device may be crucial for the health of these subjects.

Referring to FIG. 1, aspects and embodiments leverage the fact that focused ultrasound (US) stimulation of the spleen activates the same anti-inflammatory pathway triggered by VNS. This is possible due to the mechanosensitive piezo receptors we have in the nervous system. Ultrasound stimulation modulates the mechanosensative ion channels through the membrane inducing an opening of the ion channels[27,28]. Through this mechanism the US activates the splenic nerve, which results in the release of norepinephrine (NE) in the vicinity of T-cells, which causes T cells to release acetylcholine (Ach), resulting in the suppression of cytokine production. Specifically, ACh crosses the marginal zone and enters the red pulp where it interacts with α7 nAChR expressed on cytokine producing macrophages to reduce cytokine production. This the mechanistic pathway that embodiments of the wearable device target, without the subjects needing to have any a priori knowledge.

Aspects and embodiments provide an individualized and adaptive system that integrates biomarker monitoring with ultrasound stimulation.

Figure 2:
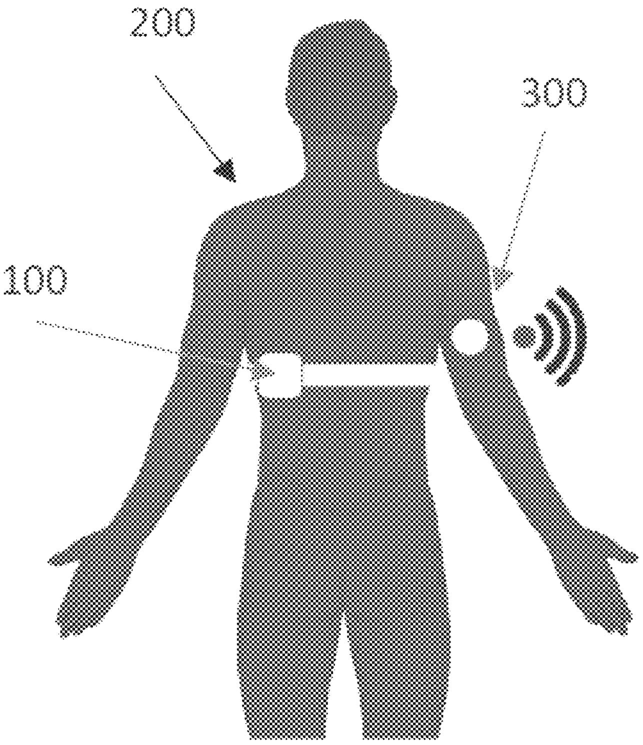
FIG. 2 is a diagram illustrating one example of a wearable device on a person, according to some embodiments.

FIG. 2 is a diagram illustrating one example of a summary of the components of a system according to certain embodiments. The system includes a wearable device 100 that can be worn by a subject 200, as discussed above. In certain examples, this device may be handheld instead of wearable. The wearable ultrasound device 100 can be integrated into a belt, vest or other item of clothing that is worn by the subject 200 for a specified time period, e.g., for a daily 1 min-1 hour treatment. The time period for which the subject wears and/or uses the device may vary depending on a variety of factors, such as the subject's condition, the type of treatment, or other factors, and is not limited to the example above. The belt, or other item of clothing or housing holding the ultrasound device, may indicate to the subject the proper positioning of the device, such that the device can be used for treatment by the subject at home.

According to certain embodiments, the wearable device 100 has a built-in focused ultrasound device, that is adjusted and placed on the body to target the nerves on and around the spleen to dampen the immune system via the above mechanism of action also illustrated in FIG. 1. According to certain embodiments, the device could be a closed-loop system that integrates biomarker monitoring and feeds into recommended ultrasound sessions via a closed-loop system to subjects with kidney transplants to prevent chronic or acute kidney rejection. Accordingly, the wearable device 100 may include a biomarker device 300, as discussed further below with reference to FIG. 3. The wearable device 100 includes an ultrasound stimulation module that is designed in a variety of different housings making it innovative and easy to adjust to the subject's needs and allows the safe use of the device at home. For example, three different housings that make the ultrasound transducer wearable include 1) a belt device, 2) a patch, and 3) a back brace/garment, but could also include any other form of clothing that will keep the ultrasound in place.

The system may further include a communications/monitoring module 300 that may be separate from the wearable device 100 or may be integrated with the wearable device 100. The communications module 300 allows remote communication, either directly or via a cloud platform or other intermediary, with the subject's (e.g., patient's) physician, and may allow for remote adjustment of one or more parameters of the device, as discussed above.

An example of the wearable device 100 implemented in a belt housing is shown in FIG. 2. According to one embodiment, in the belt form, the wearable device 100 has the ultrasound transducer embedded in the belt, so that it fits around the lower chest, with the ultrasound transducer targeting the spleen from the posterior of the body (FIG. 2). The targeted location is benchmarked with an anatomical landmark, such as the ribcage and can be adjusted and personalized to every subject by the physician, so that the size and place is always the same, and the subject can repeat the placement based on images and landmarks.

Figure 3:
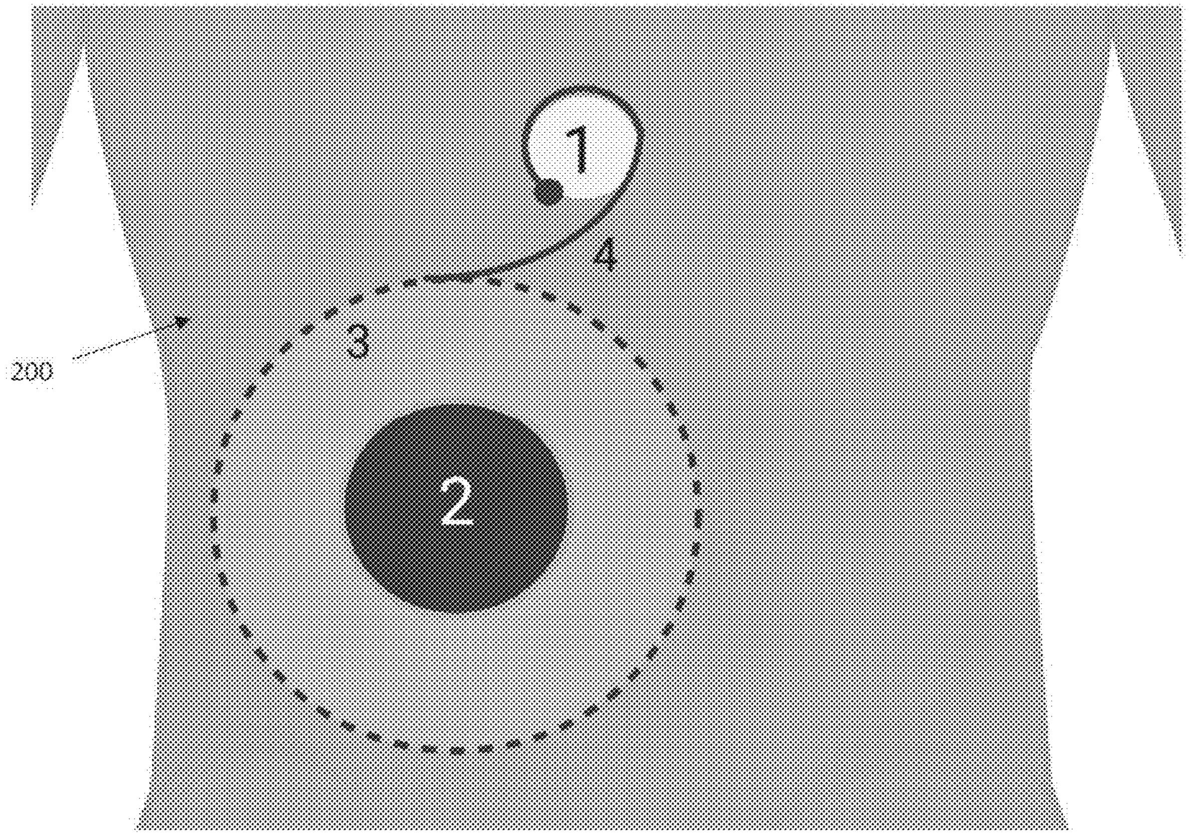
FIG. 3 is a diagram illustrating an example of the wearable device, according to some embodiments.

An example of the wearable device 100 implemented as a patch device is shown in FIG. 3. In one embodiment, the patch device is in the form of a stick-on that is directly placed on back targeting the spleen. The patch has the ultrasound transducer embedded. The consistency and reliability of adding the patch in the same place every time may be directed by a diagnostic device, such as a functioning or non-functioning biomarker device or even through ultrasound reflection that is used as a landmark for placement of the ultrasound device see illustration on FIG. 3). In one example, a biomarker device that monitors and at the same time is used as a landmark (1) may be placed in the same repeatable location to target the spleen. According to one embodiment, a stimulating ultrasound device (2) is placed on an attachable glue patch (3) that can be easily attached to the skin for treatment. In order to make sure that the therapeutic ultrasound device (2) is placed exactly on the spleen, a small either functioning or non-functioning biomarker device (1) that has a magnetic hook (or similar) is placed semi-permanently on the subject's back. This biomarker device may be a plastic device with minimal invasion to the subject (similar to how permanent glucose monitors work today). It contains a magnetic hook (4) or similar, to make sure when the therapeutic ultrasound needs to be placed for treatment, the ultrasound (2) attached to a glue patch (3) is always placed in the same position. The semi-permanent biomarker device (1) with the hook (4) attaches itself to the ultrasound device (2) through a magnetic hook or similar, making sure it is placed in the same position repeatedly. It can be used to ensure that the subject can easily attach the device in the comfort of their own home. The biomarker device in certain examples is non-functioning, but may in other examples contain micro-needles that can measure different cytokine levels or other markers. The device is minimally invasive and made of plastic and may be configured to be worn in place for an extended period of time, for example, at least 30 days.

Figure 4A:
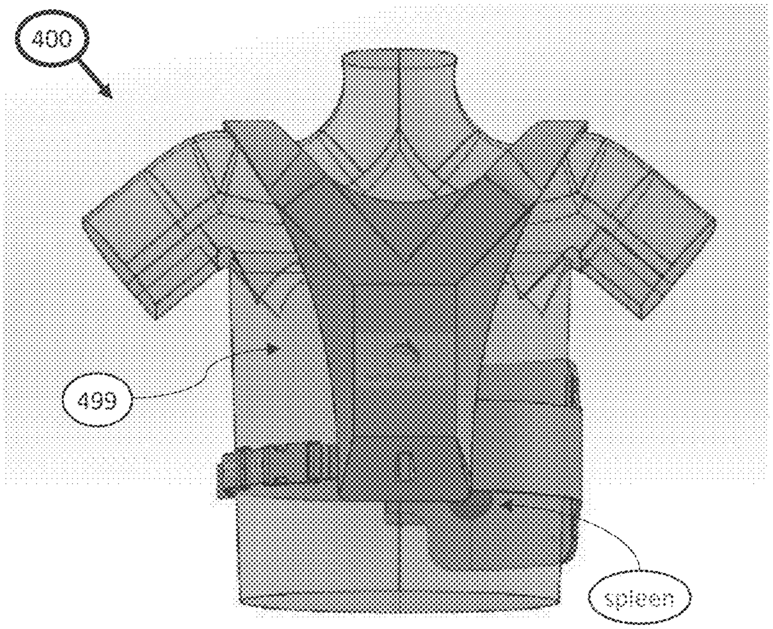
FIG. 4A shows a front view of a harness on a subject, according to some embodiments.

FIG. 4A shows a front view of a harness 400 on a subject 499, according to some embodiments. As shown, the harness 400 is worn over the torso of subject 499. In some embodiments, the subject 499 may wear a shirt or other garment under the harness 400. In some embodiments, the subject 499 may wear the harness 400 directly on the skin with no garment underneath.

Figure 4B:
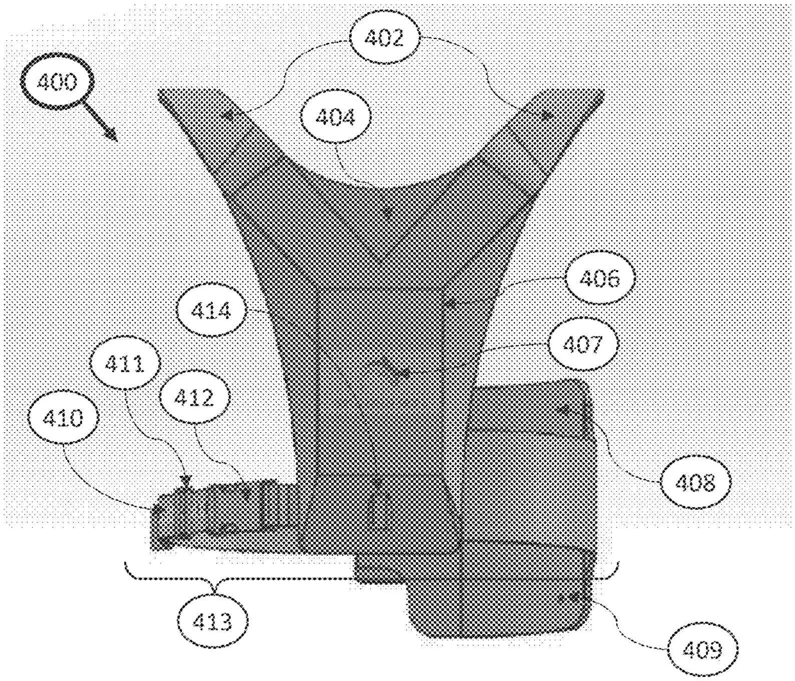
FIG. 4B shows a front view of a harness, according to some embodiments.

FIG. 4B shows a front view of a harness 400, according to some embodiments. As shown, harness 400 includes adjustable shoulder straps 402, elastic panel 404, front panel 406, power pocket 407, power pocket outlet 414, transducer securing portion 408, transducer securing portion outlet 409, adjustable waist strap 413, waist strap scale 410, waist strap clip 411, and waist strap buckle 412.

As shown, adjustable shoulder straps 402 include two straps that may be supported by or positioned over the shoulders of the subject. The adjustable shoulder straps 402 may be connected to the front panel 406. The method of connection may be, for example, and without limitations, directly molding or sewing the adjustable shoulder straps 402 and the front panel 406 together, connecting by buckle, fastening by VELCRO®, etc. The adjustable shoulder straps 402 may include padding or other cushioning features to enhance the subject's comfort. In some embodiments, the adjustable shoulder straps 402 may be made of an elastic material, an inelastic material, or a combination of two or more materials. The material may be, for example, and without limitations, canvas, plastic, elastane, etc. In some embodiments, the shoulder straps can be antibacterially and/or antimicrobially coated. For example, the coating may comprise one or more of isothiazolinone treatments, zinc pyrithione, silver, and quaternary ammonium compounds. Any coating may also be used on other portions of the wearable harness as well. In some embodiments, the material of the shoulder straps is not stretchable. In some embodiments, the adjustable shoulder straps 402 may be removable and washable. In some embodiments, the two adjustable shoulder straps may be connected together. As shown in FIG. 4B, an elastic panel 404 may connect the two adjustable shoulder straps 402 together. Alternatively, one or more adjustable horizontal straps may connect the two adjustable shoulder straps 402 together to further adjust how the harness 400 fits on the subject's body. Alternatively, the two adjustable shoulder straps 402 may merge into a single strap before they attach to the front panel 406. The adjustable shoulder straps 402 may be adjusted in length to fit subjects of different heights, sizes, and body shapes.

As shown, elastic panel 404 includes a panel made of an elastic material that connects the adjustable shoulder straps 402 to each other and/or to the top of front panel 406. The method of connection may be, for example, and without limitations, directly molding or sewing the elastic panel 404 to the adjustable shoulder straps 402 and the front panel 406, connecting by buckle, fastening by VELCRO®, etc. The elastic panel 404 may be V-shaped, triangle-shaped, or another shape. In some embodiments, the elastic panel 404 may be removable and washable. In some embodiments, such as if the two adjustable shoulder straps 402 merge into a single strap before they attach to the front panel 406, the elastic panel 404 may not connect to the front panel 406 or may be absent entirely. In some embodiments, the elastic panel 404 allows the harness to be more easily adjustable to different sized subject. For example, the elastic panel 404 ensures that the harness will fit narrow- and wide-shouldered subjects, such that, regardless of body shape, the harness is tightly fitted and snug to the subject's body.

As shown, front panel 406 includes a panel that covers at least a portion of the front of the subject's torso. As used herein, "front panel" may also be referred to as "front portion." In some embodiments, the front panel 406 may be made of an elastic material, an inelastic material, or a combination of two or more materials. The material may be, for example, and without limitations, canvas, plastic, elastane, etc. In some embodiments, the front panel 406 may be removable and washable. In some embodiments, the shape of the front panel 406 can be any shape that fits over the subject's torso, for example, but not limited to, a rectangular shape, a circular shape, a X-shape, a Y-shape, etc. The front panel 406 may be flat, or alternatively, it may be contoured to match the shape of the subject's body. In some embodiments, the front panel 406 may cover most of the subject's torso. Alternatively, in some embodiments, the front panel 406 may be shaped like a belt that provides minimal coverage of the subject's torso. Front panel 406 may include a power pocket 407.

As shown, power pocket 407 includes a pocket that can hold a power pack on the harness 400. The power pocket 407 may be sewn or otherwise attached onto the front panel 406. Alternatively, in some embodiments, power pocket 407 may not be attached to front panel 406 but may instead be attached to a different location on the harness, such as an adjustable shoulder strap 402, an adjustable waist strap 413, or a rear panel 516 (see FIG. 5). In some embodiments, the shape of the power pocket 407 may be rectangular to match the dimensions of a rectangular power pack. Alternatively, in some embodiments, the shape of the power pocket 407 can be any shape that either matches or does not match the dimensions of the power pack, so long as the power pack is not larger than the harness 400. In some embodiments, the power pocket 407 may be open on its top side and sealed on the other sides. In such embodiments, the power pack can be placed inside the power pocket 407 from its open top side and held in position by gravity. Alternatively, in some embodiments, the power pocket 407 may include securable fastenings on the interior of the pocket, so that the power pack can be placed inside the power pocket 407 and then secured by the fastenings. In such embodiments, the power pack can be removed from the power pocket 407 of harness 400 so that the harness 400 can be washed or cleaned. Power pocket 407 may include a power pocket outlet 414.

As shown, power pocket outlet 414 includes an opening through which a power cable can extend into power pocket 407. The size of this opening may vary, so long as it is large enough for the power cable to extend through but no larger than the size of the power pack. The power pocket outlet 414 may be located near the bottom, side, center, or another area of power pocket 407.

As shown, transducer securing portion 408 includes a pocket that can hold a transducer case assembly on the harness 400. In some embodiments, the transducer securing portion 408 secures the transducer case assembly in one position to prevent the transducer from moving or falling off the harness 400. In such embodiments, the transducer case assembly can be repositioned and resecured if necessary. The transducer securing portion 408 may be sewn or otherwise attached onto the adjustable waist strap 413. Alternatively, in some embodiments, transducer securing portion 408 may not be attached to adjustable waist strap 413 but may instead be attached to a different location on the harness, such as an adjustable shoulder strap 402, a front panel 406, or a rear panel 516 (see FIG. 5). The interior of the transducer securing portion 408 may include a fastening mechanism—such as a pop-lock, a magnet, VELCRO®, locking pins, clips, or a key-in-arms mechanism—to secure the transducer case assembly within the transducer securing portion 408. The exterior material of the transducer securing portion 408 may be rigid so that it does not fold or curl around the transducer case assembly. In some embodiments, the material of the transducer securing portion 408 may be transparent so that the transducer case assembly is visible within the pocket. In some embodiments, the shape of the transducer securing portion 408 may be circular to match the dimensions of a circular transducer case assembly. Alternatively, in some embodiments, the shape of the transducer securing portion 408 can be any shape that either matches or does not match the dimensions of the transducer case assembly pack. In some embodiments, the transducer securing portion 408 may be open on its top side and sealed on the other sides. In such embodiments, the transducer case assembly can be placed inside the transducer securing portion 408 from its open top side and held in position by gravity. Alternatively, in some embodiments, the transducer securing portion 408 may include securable fastenings on the interior of the pocket, so that the transducer case assembly can be placed inside the transducer securing portion 408 and then secured by the fastenings. In such embodiments, the transducer case assembly can be removed from the transducer securing portion 408 of harness 400 so that the harness 400 can be washed or cleaned. In some embodiments, the transducer securing portion 408 may include a transducer securing portion scale to assist in the placement of the transducer case assembly. Transducer securing portion 408 may include a transducer securing portion outlet 409.

As shown, transducer securing portion outlet 409 includes an opening through which a power cable can extend into transducer securing portion 408. The size of this opening may vary, so long as it is large enough for the power cable to extend through but no larger than the size of the transducer case assembly. The transducer securing portion outlet 409 may be located near the bottom, side, center, or another area of transducer securing portion 408.

As shown, adjustable waist strap 413 includes a horizontal strap that may be supported by or positioned over the waist. The adjustable waist strap 413 may be connected to the front panel 406 by waist strap buckle 412. Alternatively, the method of connection may be, for example, and without limitations, directly molding or sewing the adjustable waist strap 413 and the front panel 406 together, fastening by VELCRO®, etc. The adjustable waist strap 413 may include padding or other cushioning features to enhance the subject's comfort. In some embodiments, the adjustable waist strap 413 may be inelastic to ensure a consistent fit of the harness 400 along the subject's waist. In such embodiments, the adjustable waist strap 413 may be made of one or more inelastic materials. The material may be, for example, and without limitations, canvas, plastic, etc. so long as the material is inelastic. In some embodiments, the adjustable waist strap 413 may be removable and washable. In some embodiments, one or more adjustable horizontal straps may run parallel to the adjustable waist strap 413 to further adjust how the harness 400 fits on the subject's body. In these embodiments, the one or more adjustable horizontal straps may be connected to the adjustable waist strap 413 or may merge into a single strap before it attaches to the front panel 406 via the waist strap buckle 412. The adjustable waist strap 413 may be adjusted in length to fit subjects of different heights, sizes, and body shapes and can be replaced if necessary. For example, if the subject is too small or large for the harness 400 and adjustable waist strap 413 no longer fits the subject, it may be replaced by an adjustable waist strap 413 of a different length. In some embodiments, in order to cover a greater region of the patient's torso, such as the region including the spleen, one side of the adjustable waist strap 413 may be wider than the other side. Adjustable waist strap 413 may include a waist strap scale 410, a waist strap clip 411, and/or a waist strap buckle 412.

As shown, waist strap scale 410 includes a scale that extends lengthwise along the adjustable waist strap 413. This scale allows the adjustable waist strap 413 to be adjusted to a set length every time harness 400 is worn. The line markers of waist strap scale 410 may be printed, embroidered, etched, or otherwise attached to the adjustable waist strap 413. The waist strap scale 410 may use metric, imperial, or other units of distance measurement. In some embodiments, waist strap scale 410 extends in only one dimension. The waist strap scale 410 may extend across the entire length of adjustable waist strap 413, or alternatively, it may extend across only part of the length.

As shown, waist strap clip 411 includes a clip that attaches to adjustable waist strap 413 and holds the strap in place near the waist strap buckle 412. In some embodiments, the waist strap clip 411 is rectangular in shape and hollow in the middle so that the waist strap scale 413 is still visible. Alternatively, in some embodiments, the waist strap clip 411 may be any shape, for example, but not limited to, circular, triangular, organic, etc. In some embodiments, the waist strap clip 411 may include a clip pointer that extends partway along the middle so that the clip pointer can align with line markers of the waist strap scale 413. In such embodiments, the clip pointer can be used to read the waist strap scale 413. In some embodiments, more than one clip pointer may be attached to waist strap clip 411, such that the central axes of each clip pointer are parallel to the line markers of the waist strap scale 413 and parallel to each other.

As shown, waist strap buckle 412 includes a buckle that attaches the adjustable waist strap 413 to the front panel 406. The waist strap buckle 412 can be opened when the subject is putting on the harness 400, then closed to secure the harness 400 around the subject. In some embodiments, the waist strap buckle 412 may be a side release buckle. Alternatively, in some embodiments, the waist strap buckle 412 may be any type of fastener, for example, but not limited to, a tie buckle, snap buckle, roller buckle, ratchet buckle, cam buckle, etc. The material of waist strap buckle 412 may be, for example, and without limitations, metal, plastic, etc.

Figure 5:
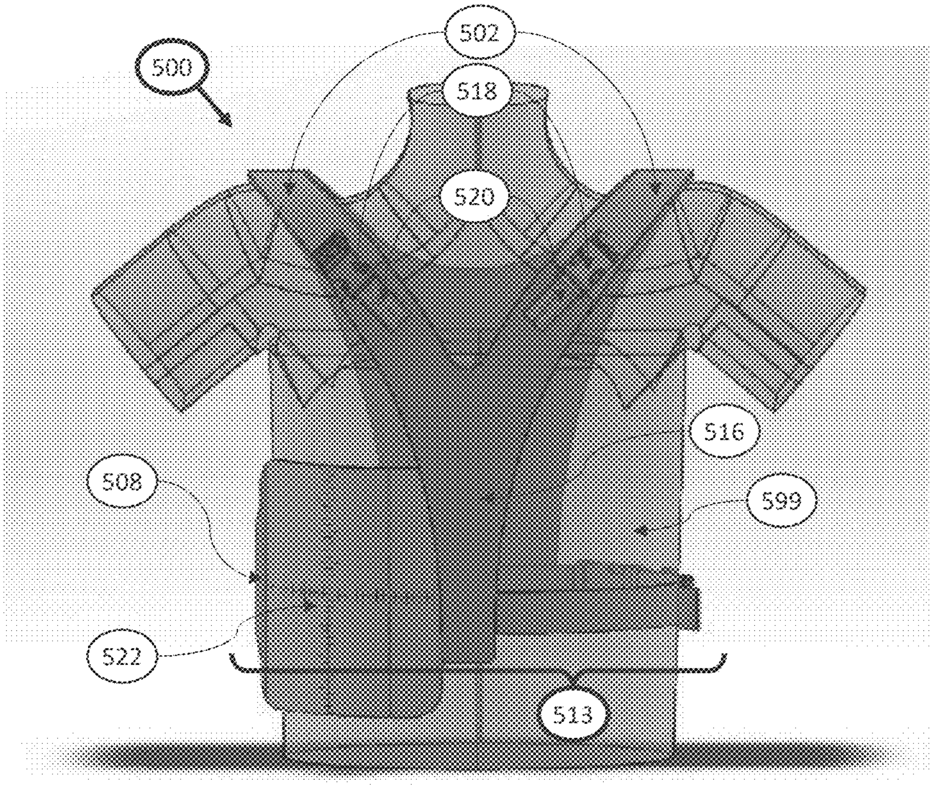
FIG. 5 shows a rear view of a harness on a subject, according to some embodiments.

FIG. 5 shows a rear view of a harness 500 on a subject 599, according to some embodiments. As shown, FIG. 5 includes adjustable shoulder straps 502, shoulder strap buckles 518, shoulder strap scales 520, rear panel 516, adjustable waist strap 513, transducer securing portion 508, and transducer securing portion scale 522.

As shown, adjustable shoulder straps 502 include two straps that may be supported by or positioned over the shoulders of the subject 599. In some embodiments, the connection region between the adjustable shoulder straps 502 and the rear panel 516 may comprise adjustable clasps. In such embodiments, the adjustable clasps may include shoulder strap buckles 518. In such embodiments, the adjustable clasps may be configured to connect and disconnect and adjust the connection positions between the adjustable shoulder straps 502 and the rear panel 516. The connection positions may comprise an overlap region between the adjustable shoulder straps 502 and the rear panel 516. Alternatively, the connection positions may comprise no overlap region between the adjustable shoulder straps 502 and the rear panel 516. Alternatively, the method of connection may be, for example, and without limitations, directly molding or sewing the adjustable shoulder straps 502 and the rear panel 516 together, fastening by VELCRO®, etc. The adjustable shoulder straps 502 may include padding or other cushioning features to enhance the comfort of the subject 599. In some embodiments, the adjustable shoulder straps 502 may be made of an elastic material, an inelastic material, or a combination of two or more materials. The material may be, for example, and without limitations, canvas, plastic, elastane, etc. In some embodiments, the adjustable shoulder straps 502 may be removable and washable. In some embodiments, the two adjustable shoulder straps may be connected together. In some embodiments, one or more adjustable horizontal straps may connect the two adjustable shoulder straps 502 together to further adjust how the harness 500 fits on the body of subject 599. Alternatively, the two adjustable shoulder straps 502 may merge into a single strap before they attach to the rear panel 516. The adjustable shoulder straps 502 may be adjusted in length to fit subjects of different heights, sizes, and body shapes. However, in some embodiments, if the subject 599 is too small or large for the harness 500, the adjustable shoulder straps 502 may no longer be able to fit the subject.

As shown, shoulder strap buckles 518 include two buckles that attach the adjustable shoulder straps 502 to the rear panel 516. One end of each shoulder strap buckle 518 may be attached to an adjustable shoulder strap 502; the other end may be attached to the rear panel 516, so that when the buckle is closed, the adjustable shoulder straps 502 are attached to the rear panel 516. In some embodiments, one or both ends of each shoulder strap buckle 518 may be attached to a shoulder strap scale 520. In some embodiments, the shoulder strap buckles 518 may be side release buckles. Alternatively, in some embodiments, the shoulder strap buckles 518 may be any type of fastener, for example, but not limited to, tie buckles, snap buckles, roller buckles, ratchet buckles, cam buckles, etc. The material of shoulder strap buckles 518 may be, for example, and without limitations, metal, plastic, etc.

As shown, shoulder strap scales 520 include scales that extend lengthwise along the adjustable shoulder straps 502. These scales allow the adjustable shoulder straps 502 to be adjusted to a set length every time harness 500 is worn. The line markers of shoulder strap scales 520 may be printed, embroidered, etched, or otherwise attached to the adjustable shoulder straps 502. The shoulder strap scales 520 may use metric, imperial, or other units of distance measurement. In some embodiments, the shoulder strap scales 520 extend in only one dimension. In some embodiments, a shoulder strap scale 520 may be attached to a shoulder strap buckle 518. The shoulder strap scales 520 may extend across the entire length of adjustable shoulder straps 502, or alternatively, they may extend across only part of the length.

As shown, rear panel 516 includes a panel that covers at least a portion of the back of the subject's torso. As used herein, "rear panel" may also be referred to as "rear portion." In some embodiments, the rear panel 516 may be inelastic to ensure a consistent fit of the harness 500 along the back of the subject's torso. In such embodiments, the rear panel 516 may be made of one or more inelastic materials. The material may be, for example, and without limitations, canvas, plastic, etc. so long as the material is inelastic. In some embodiments, the rear panel 516 may be removable and washable. In some embodiments, the shape of the rear panel 516 can be any shape that fits over the subject's torso, for example, but not limited to, a rectangular shape, a circular shape, a X-shape, a Y-shape, etc. The rear panel 516 may be flat, or alternatively, it may be contoured to match the shape of the subject's body. In some embodiments, the rear panel 516 may cover most of the subject's torso. Alternatively, in some embodiments, the rear panel 516 may be shaped like a belt that provides minimal coverage of the subject's torso. One end of each shoulder strap buckle 518 may be attached to the rear panel 516, so that when the buckle is closed, the adjustable shoulder straps 502 are attached to the rear panel 516.

As shown, adjustable waist strap 513 includes a horizontal strap that may be supported by or positioned over the waist. The adjustable waist strap 513 may be connected to the rear panel 516. The method of connection may be, for example, and without limitations, directly molding or sewing the adjustable waist strap 513 and the rear panel 516 together, connecting by buckle, fastening by VELCRO®, etc. The adjustable waist strap 513 may include padding or other cushioning features to enhance the subject's comfort. In some embodiments, the adjustable waist strap 513 may be inelastic to ensure a consistent fit of the harness 500 along the subject's waist. In such some embodiments, the adjustable waist strap 513 may be made of one or more inelastic materials. The material may be, for example, and without limitations, canvas, plastic, elastane, etc. so long as the material is inelastic. In some embodiments, the adjustable waist strap 513 may be removable and washable. In some embodiments, one or more adjustable horizontal straps may run parallel to the adjustable waist strap 513 to further adjust how the harness 500 fits on the subject's body. In these embodiments, the one or more adjustable horizontal straps may be connected to the adjustable waist strap 513 or may merge into a single strap before it attaches to the rear panel 516. The adjustable waist strap 513 may be adjusted in length to fit subjects of different heights, sizes, and body shapes and can be replaced if necessary. For example, if the subject is too small or large for the harness 500 and adjustable waist strap 513 no longer fits the subject, it may be replaced by an adjustable waist strap 513 of a different length. In some embodiments, in order to cover a greater region of the patient's torso, such as the region including the spleen, one side of the adjustable waist strap 513 may be wider than the other side. Adjustable waist strap 513 may include a waist strap scale, a waist strap clip, and/or a waist strap buckle.

As shown, transducer securing portion 508 includes a pocket that can hold a transducer case assembly on the harness 500. In some embodiments, the transducer securing portion 508 secures the transducer case assembly in one position to prevent the transducer from moving or falling off the harness 500. In such embodiments, the transducer case assembly can be repositioned and resecured if necessary. The transducer securing portion 508 may be sewn or otherwise attached onto the adjustable waist strap 513. Alternatively, in some embodiments, transducer securing portion 508 may not be attached to adjustable waist strap 513 but may instead be attached to a different location on the harness, such as an adjustable shoulder strap 502, a front panel 406 (see FIG. 4B), or a rear panel 516. The interior of the transducer securing portion 508 may include a fastening mechanism—such as a pop-lock, a magnet, VELCRO®, locking pins, clips, or a key-in-arms mechanism—to secure the transducer case assembly within the transducer securing portion 508. The exterior material of the transducer securing portion 508 may be rigid so that it does not fold or curl around the transducer case assembly. In some embodiments, the material of the transducer securing portion 508 may be transparent so that the transducer case assembly is visible within the pocket. In some embodiments, the shape of the transducer securing portion 508 may be circular to match the dimensions of a circular transducer case assembly. Alternatively, in some embodiments, the shape of the transducer securing portion 508 can be any shape that either matches or does not match the dimensions of the transducer case assembly pack. In some embodiments, the transducer securing portion 508 may be open on its top side and sealed on the other sides. In such embodiments, the transducer case assembly can be placed inside the transducer securing portion 508 from its open top side and held in position by gravity. Alternatively, in some embodiments, the transducer securing portion 508 may include securable fastenings on the interior of the pocket, so that the transducer case assembly can be placed inside the transducer securing portion 508 and then secured by the fastenings. In such embodiments, the transducer case assembly can be removed from the transducer securing portion 508 of harness 500 so that the harness 500 can be washed or cleaned. Transducer securing portion 508 may include a transducer securing portion scale 522 to assist in the placement of the transducer case assembly.

As shown, transducer securing portion scale 522 includes a two-dimensional scale that extends lengthwise and heightwise along the exterior of the transducer securing portion 508. This scale may be used to align the transducer case assembly so that it may be placed in the same position inside the transducer securing portion 508 every time harness 500 is worn. The line markers of transducer securing portion scale 522 may be printed, embroidered, etched, or otherwise attached to the transducer securing portion 508. transducer securing portion scale 522 may use metric, imperial, or other units of distance measurement. The transducer securing portion scale 522 may extend across the entire exterior surface area of transducer securing portion 508, or alternatively, it may extend across only part of the surface area. In some embodiments, transducer securing portion scale 522 may extend farther in one dimension than the other. In some embodiments, the transducer securing portion scale 522 may be a grid that extends across the entire exterior surface area of the transducer securing portion 508.

Figure 6:
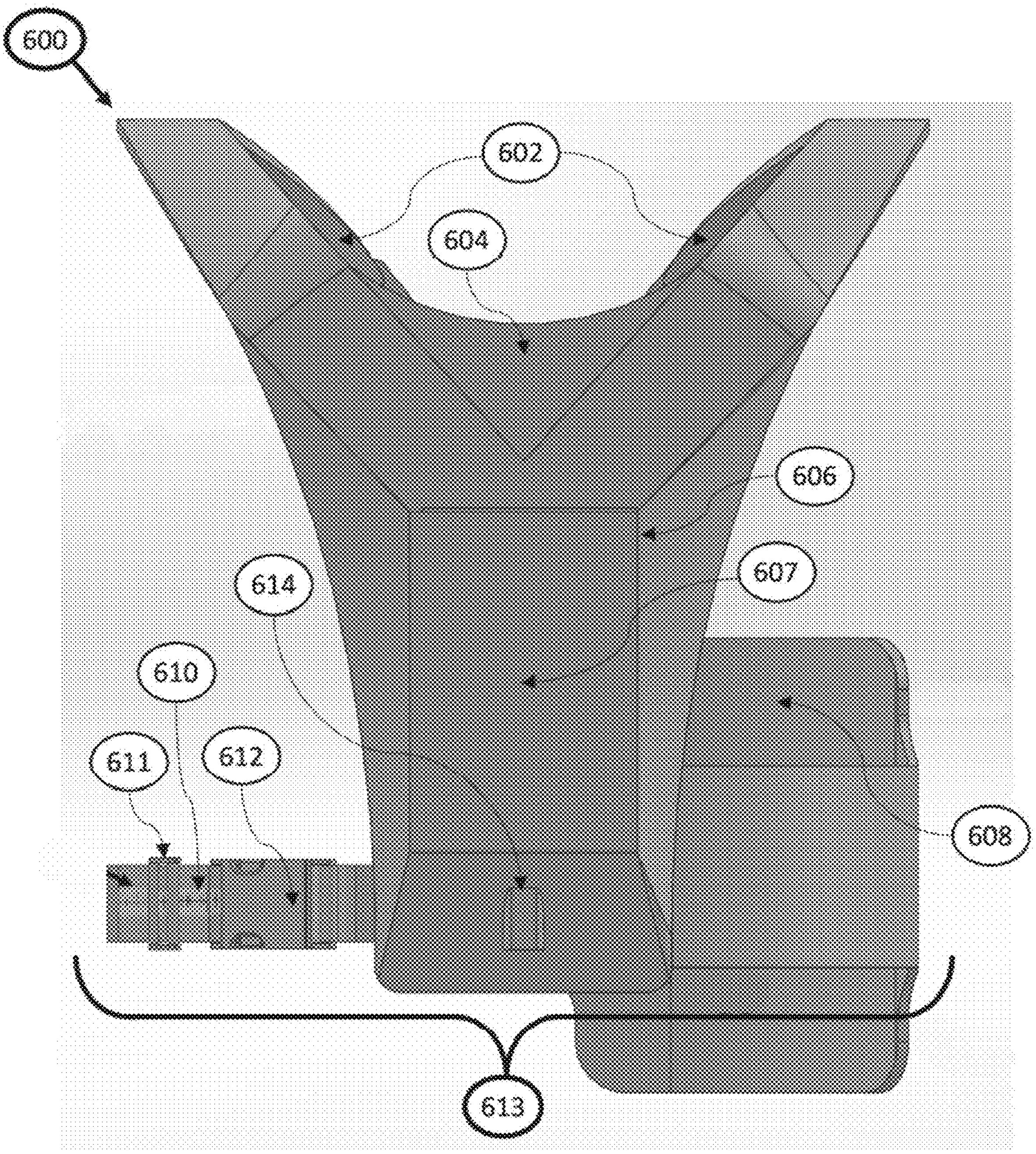
FIG. 6 shows a front view of a harness, according to some embodiments.

FIG. 6 shows a front view of a harness 600, according to some embodiments. As shown, FIG. 6 includes adjustable shoulder straps 602, elastic panel 604, front panel 606, power pocket 607, power pocket outlet 614, transducer securing portion 608, adjustable waist strap 613, waist strap scale 610, waist strap clip 611, and waist strap buckle 612.

As shown, adjustable shoulder straps 602 include two straps that may be supported by or positioned over the shoulders. Shoulder straps 602 can include any features of shoulder straps 402 of FIG. 4B and/or 502 of FIG. 5.

As shown, elastic panel 604 includes a panel made of an elastic material that connects the adjustable shoulder straps 602 to each other and/or to the top of front panel 606. Elastic panel 604 can include any features of elastic panel 404 of FIG. 4B.

As shown, front panel 606 includes a panel that covers at least a portion of the front of the subject's torso. Front panel 606 can include any features of front panel 406 of FIG. 4B.

As shown, power pocket 607 includes a pocket that can hold a power pack on the harness 600. Power pocket 607 can include any features of power pocket 407 of FIG. 4B.

As shown, power pocket outlet 614 includes an opening through which a power cable can extend into power pocket 607. Power pocket outlet 614 can include any features of power pocket outlet 414 of FIG. 4B.

As shown, transducer securing portion 608 includes a pocket that can hold a transducer case assembly on the harness 600. Transducer securing portion 608 can include any features of transducer securing portion 408 of FIG. 4B and/or 508 of FIG. 5.

As shown, adjustable waist strap 613 includes a horizontal strap that may be supported by or positioned over the waist. Adjustable waist strap 613 can include any features of adjustable waist strap 413 of FIG. 4B and/or 513 of FIG. 5.

As shown, waist strap scale 610 includes a scale that extends lengthwise along the adjustable waist strap 613. Waist strap scale 610 can include any features of waist strap scale 410 of FIG. 4B.

As shown, waist strap clip 611 includes a clip that attaches to adjustable waist strap 613 and holds the strap in place near the waist strap buckle 612. Waist strap clip 611 can include any features of waist strap clip 411 of FIG. 4B.

As shown, waist strap buckle 612 includes a buckle that attaches the adjustable waist strap 613 to the front panel 606. Waist strap buckle 612 can include any features of waist strap buckle 412 of FIG. 4B.

Figure 7:
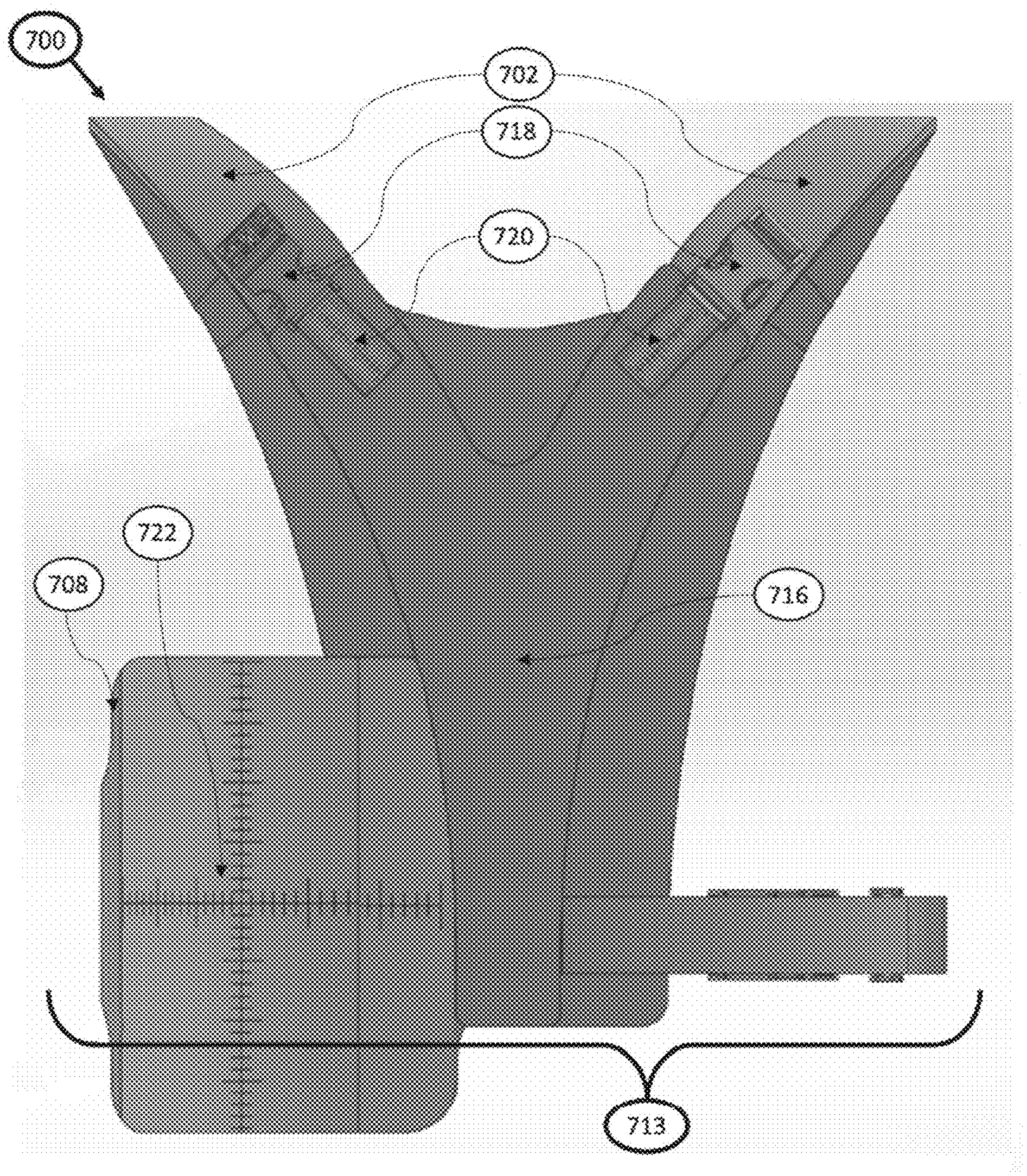
FIG. 7 shows rear view of a harness, according to some embodiments.

FIG. 7 shows a rear view of a harness 700, according to some embodiments. As shown, FIG. 7 includes adjustable shoulder straps 702, shoulder strap buckles 718, shoulder strap scales 720, rear panel 716, adjustable waist strap 713, transducer securing portion 708, and transducer securing portion scale 722.

As shown, adjustable shoulder straps 702 include two straps that may be supported by or positioned over the shoulders of the subject. Shoulder straps 702 can include any features of shoulder straps 402 of FIG. 4B, 502 of FIG. 5, and/or 602 of FIG. 6.

As shown, shoulder strap buckles 718 include two buckles that attach the adjustable shoulder straps 702 to the rear panel 716. Shoulder strap buckles 718 can include any features of shoulder strap buckles 518 of FIG. 5.

As shown, shoulder strap scales 720 include scales that extend lengthwise along the adjustable shoulder straps 702. Shoulder strap scales 720 can include any features of shoulder strap scales 520 of FIG. 5.

As shown, rear panel 716 includes a panel that covers at least a portion of the back of the subject's torso. Rear panel 716 can include any features of rear panel 516 of FIG. 5.

As shown, adjustable waist strap 713 includes a horizontal strap that may be supported by or positioned over the waist. Adjustable waist strap 713 can include any features of adjustable waist strap 413 of FIG. 4B, 513 of FIG. 5, and/or 613 of FIG. 6.

As shown, transducer securing portion 708 includes a pocket that can hold a transducer case assembly on the harness 700. Transducer securing portion 708 can include any features of transducer securing portion 408 of FIG. 4B, 508 of FIG. 5, and/or 608 of FIG. 6.

As shown, transducer securing portion scale 722 includes a two-dimensional scale that extends lengthwise and heightwise along the exterior of the transducer securing portion 708. Transducer securing portion scale 722 can include any features of transducer securing portion scale 522 of FIG. 5.

Figure 8A:
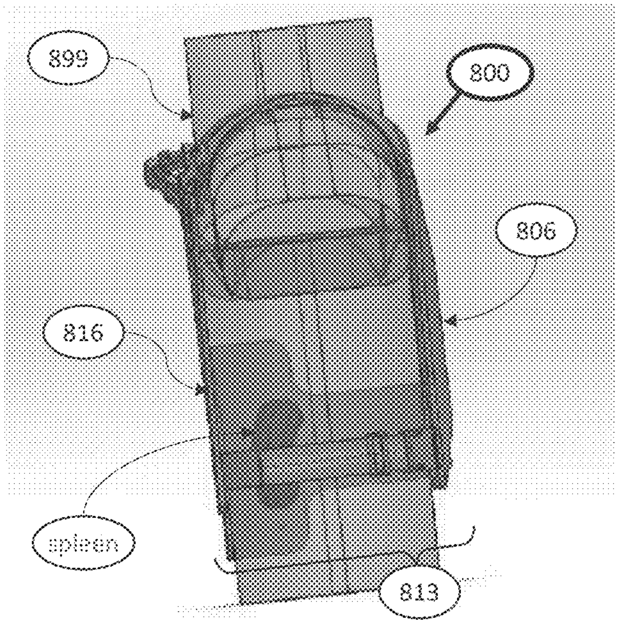
FIG. 8A shows a right side view of a harness on a subject, according to some embodiments.

FIG. 8A shows a right side view of a harness 800 on a subject 899, according to some embodiments. As shown, FIG. 8A includes front panel 806, rear panel 816, and adjustable waist strap 813. In some embodiments, the adjustable waist strap 813 may connect the front panel 806 to the rear panel 816 on the left-hand side of the subject and/or on the right-hand side of the subject. In some embodiments, the right-hand side of the adjustable waist strap 813 may be narrower than the left-hand side of the adjustable waist strap 813. As shown, the spleen is located on the left-hand side of the subject 899 proximate to the rear panel 816. Relative to a central axis drawn heightwise through subject 899, the spleen is located on approximately the same horizontal plane as the adjustable waist strap 813. Harness 800 can include any features of harness 400 of FIG. 4B, harness 500 of FIG. 5, harness 600 of FIG. 6, harness 700 of FIG. 7, and/or harness 1000 of FIG. 10.

Figure 8B:
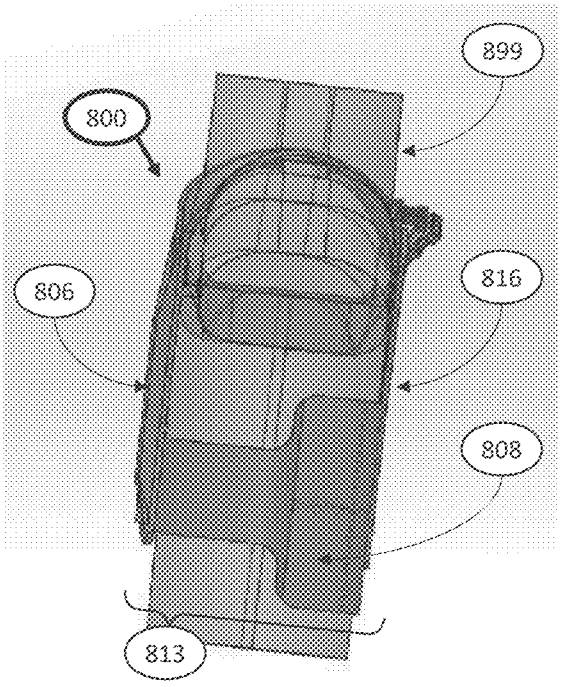
FIG. 8B shows a left side view of a harness on a subject, according to some embodiments.

FIG. 8B shows a left side view of a harness 800 on a subject 899, according to some embodiments. As shown, FIG. 8A includes front panel 806, rear panel 816, adjustable waist strap 813, and transducer securing portion 808. In some embodiments, the transducer securing portion 808 may be placed over the left-hand side of the subject 899, covering the spleen. In some embodiments, the adjustable waist strap 813 may connect the front panel 806 to the rear panel 816 on the left-hand side of the subject and/or on the right-hand side of the subject. In some embodiments, the right-hand side of the adjustable waist strap 813 may be narrower than the left-hand side of the adjustable waist strap 813. In some embodiments, the left-hand side of the adjustable waist strap 813 may be wider than the right-hand side of the adjustable waist strap 813. In such embodiments, the transducer securing portion 808 may be located on and supported by the left-hand side of the adjustable waist strap 813. Harness 800 can include any features of harness 400 of FIG. 4B, harness 500 of FIG. 5, harness 600 of FIG. 6, harness 700 of FIG. 7, and/or harness 1000 of FIG. 10.

Figure 9A:
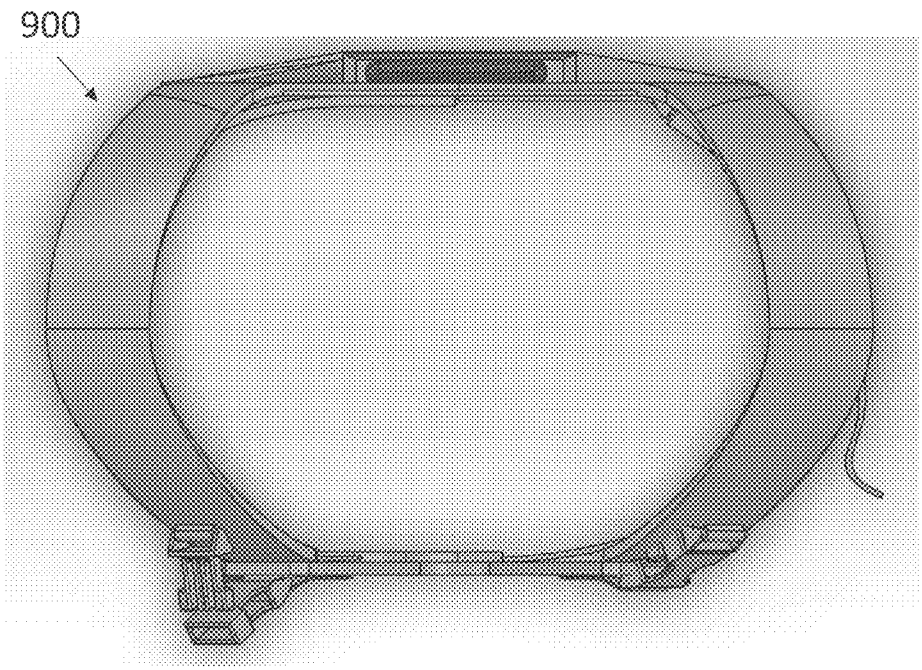
FIG. 9A is a top view of a harness, according to some embodiments.
Figure 9B:
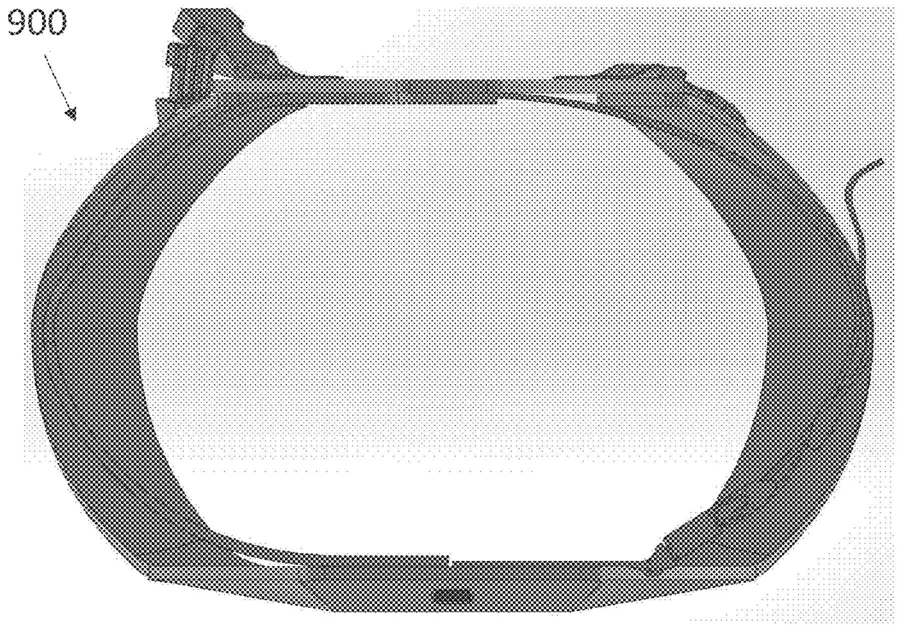
FIG. 9B is a bottom view of a harness, according to some embodiments.

FIG. 9A shows a top view of a harness 900 according to some embodiments, and FIG. 9B shows a bottom view of a harness, according to some embodiments.

Figure 10:
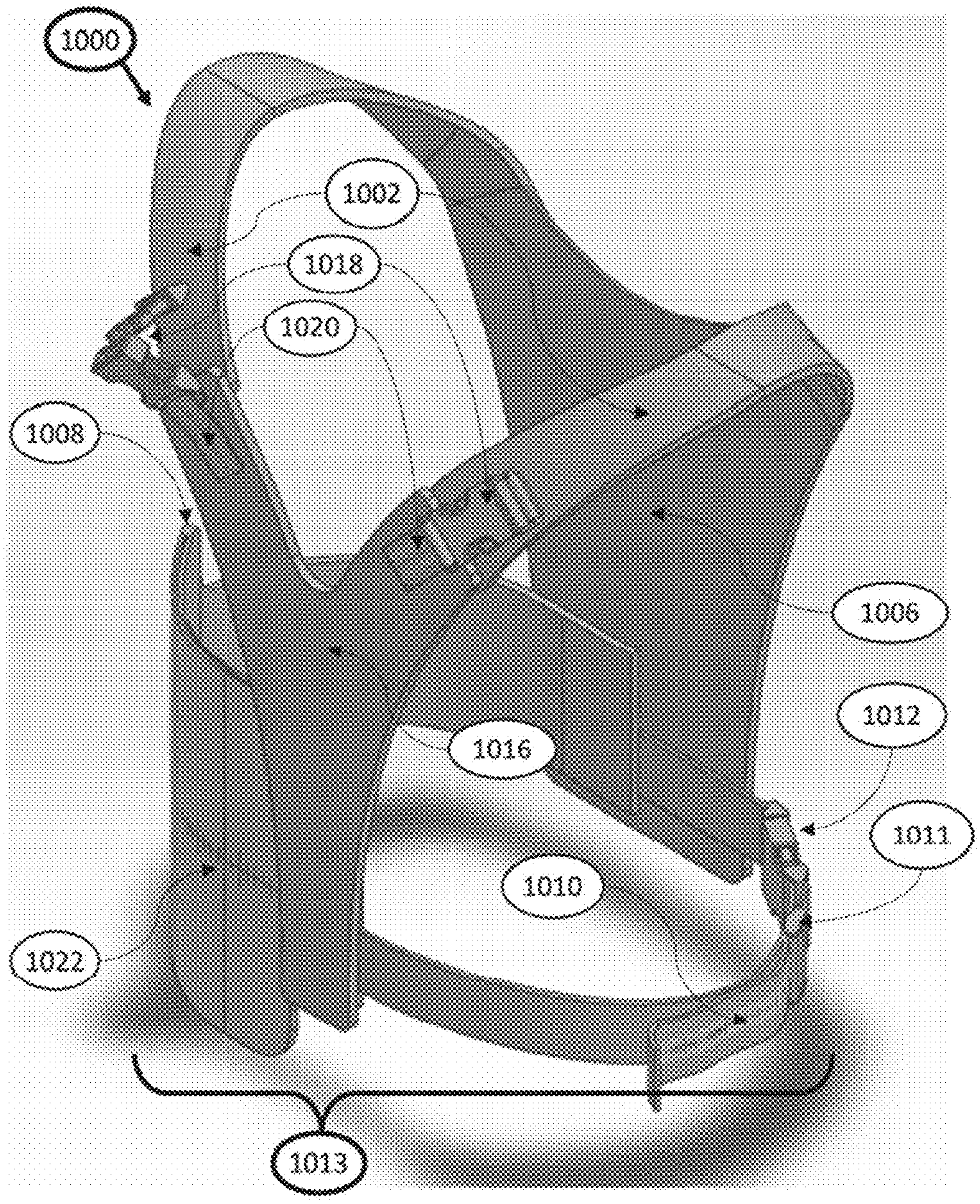
FIG. 10 shows a perspective view of a harness, according to some embodiments.

FIG. 10 shows a perspective view of a harness 1000, according to some embodiments. As shown, FIG. 10 includes adjustable shoulder straps 1002, shoulder strap buckles 1018, shoulder strap scales 1020, front panel 1006, adjustable waist strap 1013, waist strap buckle 1012, waist strap clip 1011, waist strap scale 1010, rear panel 1016, transducer securing portion 1008, and transducer securing portion scale 1022.

As shown, adjustable shoulder straps 1002 include two straps that may be supported by or positioned over the shoulders. Shoulder straps 1002 can include any features of shoulder straps 402 of FIG. 4B, 502 of FIG. 5, 602 of FIG. 6, and/or 702 of FIG. 7.

As shown, shoulder strap buckles 1018 include two buckles that attach the adjustable shoulder straps 1002 to the rear panel 1016. Shoulder strap buckles 1018 can include any features of shoulder strap buckles 518 of FIGS. 5 and/or 718 of FIG. 7.

As shown, shoulder strap scales 1020 include scales that extend lengthwise along the adjustable shoulder straps 1002. Shoulder strap scales 1020 can include any features of shoulder strap scales 520 of FIGS. 5 and/or 720 of FIG. 7.

As shown, front panel 1006 includes a panel that covers at least a portion of the front of the subject's torso. Front panel 1006 can include any features of front panel 406 of FIG. 4B and/or 606 of FIG. 6.

As shown, adjustable waist strap 1013 includes a horizontal strap that may be supported by or positioned over the waist. In some embodiments, the adjustable waist strap 1013 may connect the front panel 1006 to the rear panel 1016 on the left-hand side of the subject and/or on the right-hand side of the subject. Adjustable waist strap 1013 can include any features of adjustable waist strap 413 of FIG. 4B, 513 of FIG. 5, 613 of FIG. 6, and/or 713 of FIG. 7.

As shown, waist strap buckle 1012 includes a buckle that attaches the adjustable waist strap 1013 to the front panel 1006. Waist strap buckle 1012 can include any features of waist strap buckle 412 of FIG. 4B and/or 312 of FIG. 3.

As shown, waist strap clip 1011 includes a clip that attaches to adjustable waist strap 1013 and holds the strap in place near the waist strap buckle 1012. Waist strap clip 1011 can include any features of waist strap clip 411 of FIG. 4B and/or 611 of FIG. 6.

As shown, waist strap scale 1010 includes a scale that extends lengthwise along the adjustable waist strap 1013. Waist strap scale 1010 can include any features of waist strap scale 410 of FIG. 4B and/or 610 of FIG. 6.

As shown, rear panel 1016 includes a panel that covers at least a portion of the back of the subject's torso. Rear panel 1016 can include any features of rear panel 516 of FIGS. 5 and/or 716 of FIG. 7.

As shown, transducer securing portion 1008 includes a pocket that can hold a transducer case assembly on the harness 1000. Transducer securing portion 1008 can include any features of transducer securing portion 408 of FIG. 4B, 508 of FIG. 5, 608 of FIG. 6, and/or 708 of FIG. 7.

As shown, transducer securing portion scale 1022 includes a two-dimensional scale that extends lengthwise and heightwise along the exterior of the transducer securing portion 1008. Transducer securing portion scale 1022 can include any features of transducer securing portion scale 522 of FIGS. 5 and/or 722 of FIG. 7.

Figure 11C:
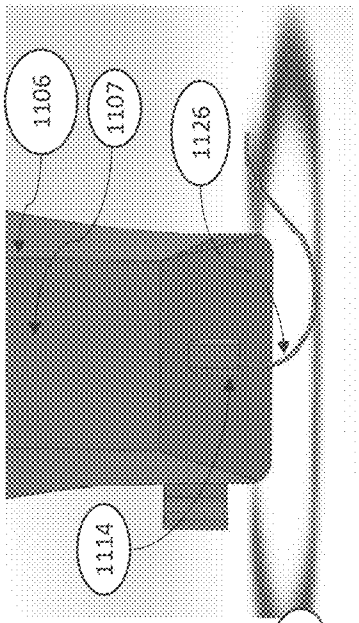
FIG. 11C shows a portion of a pocket for a power pack, according to some embodiments.
Figure 11B:
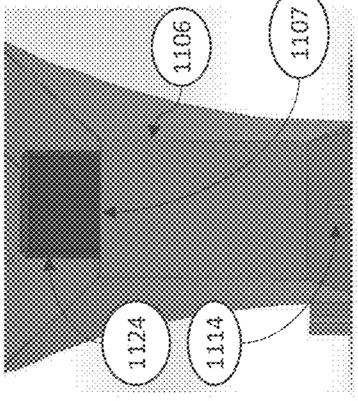
FIG. 11B shows a power pack in a pocket of a harness, according to some embodiments.
Figure 11A:
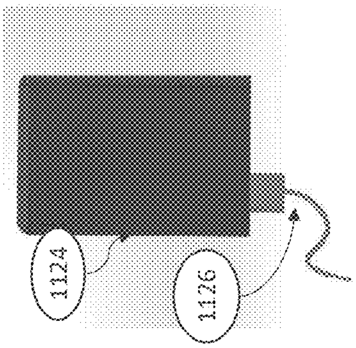
FIG. 11A shows a power pack, according to some embodiments.

FIG. 11A shows a power pack 1124, according to some embodiments. Power pack 1124 includes power cable 1126. In some embodiments, power pack 1124 may be rechargeable and may include additional ports and cables to enable recharging. In some embodiments, the power pack 1124 may be made of a hard, insulating material that protects the circuitry included within the power pack 1124. The material may be, for example, and without limitations, metal, plastic, etc. As shown, in some embodiments, power pack 1124 may be rectangular in shape. Alternatively, in some embodiments, the shape of the power pack 1124 can be any shape. In some embodiments, power cable 1126 may connect power pack 1124 to the transducer case assembly, thereby powering the transducer. In some embodiments, power cable 1126 may be a USB-A cable. Alternatively, in some embodiments, power cable 1126 may be any type of power cable, for example, but not limited to, micro-USB, USB-C, 8-pin, etc. In some embodiments, power cable 1124 may be long enough to extend around the entire circumference of a subject's torso.

FIG. 11B shows a power pack 1124 in a power pocket 1107 of a harness, according to some embodiments. As shown, the power pocket 1107 may be centrally located on a front panel 1106 of a harness. Alternatively, in some embodiments, power pocket 1107 may not be attached to front panel 1106 but may instead be attached to a different location on the harness, such as an adjustable shoulder strap, an adjustable waist strap, or a rear panel. Power pack 1124 may be placed inside the power pocket 1107. Power pocket outlet 1114 may be located at the bottom of power pocket 1107. Alternatively, in some embodiments, the power pack outlet 1114 may be located in other areas of power pocket 1107, for example, but not limited to, the top, the side, or the front. In some embodiments, the power pocket 1107 and power pack 1124 may both be rectangular in shape. Alternatively, in some embodiments, the shape of the power pocket 1107 can be any shape that either matches or does not match the dimensions of the power pack 1124. As shown, the power pocket 1107 may be open on its top side and sealed on the other sides. In such embodiments, the power pack 1124 can be placed inside the power pocket 1107 from its open top side and held in position by gravity. Alternatively, in some embodiments, the power pocket 1107 may include securable fastenings on the interior of the pocket, so that the power pack can be placed inside the power pocket 1107 and then secured by the fastenings. Although not visible in FIG. 11B, power cable 1126 may extend through power pocket outlet 1114, as depicted in FIG. 11C.

FIG. 11C shows a portion of a power pocket 1107 for a power pack 1124, according to some embodiments. As shown, this portion includes a power pocket outlet 1114 located at the bottom of the power pocket 1107, which may be centrally located on a front panel 1106 of a harness. In some embodiments, power pack outlet 1114 may not be located at the bottom of the power pocket 1107 but may instead be located elsewhere on the power pocket 1107, for example, but not limited to, the top, the side, or the front. Furthermore, in some embodiments, power pocket 1107 may not be attached to front panel 1106 but may instead be attached to a different location on the harness, such as an adjustable shoulder strap, an adjustable waist strap, or a rear panel. Power cable 1126, which may connect power pack 1124 (see FIG. 11B) to the transducer assembly 1050 (see FIG. 10B), may extend through power pocket outlet 1114. In some embodiments, power pack 1124 may provide electric power to transducer case assembly 1250 via power cable 1126. Although not visible in FIG. 11C, power pack 1124 may be placed inside the power pocket 1107, as depicted in FIG. 11B.

Figure 12A:
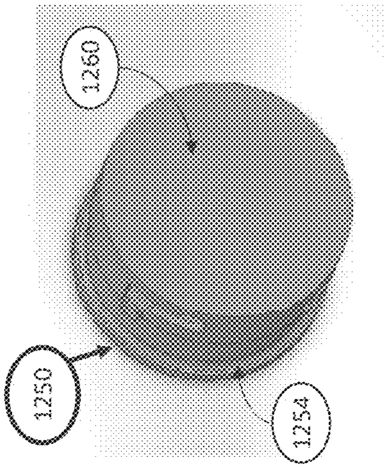
FIG. 12A shows a transducer case assembly, according to some embodiments.

FIG. 12A shows a transducer case assembly 1250, according to some embodiments. As shown, the transducer case assembly 1250 includes an interchangeable mechanical lens 1260 mounted over a transducer case 1254. Not visible in FIG. 12A but contained within the transducer case assembly 1250 is a transducer 1452 (see FIG. 14A). The transducer case assembly 1250 may be configured to couple to a transducer securing portion of the harness. Transducer case assembly 1250 can include any features of transducer case assembly 1450 of FIG. 14A.

Figure 12B:
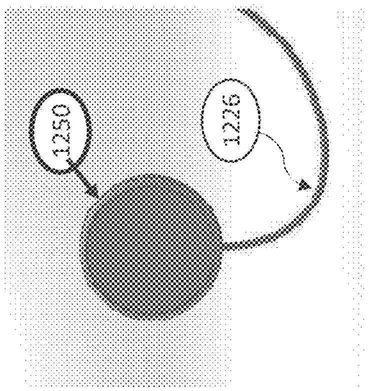
FIG. 12B shows a transducer case assembly connected to a power cable, according to some embodiments.

FIG. 12B shows a transducer case assembly 1250 connected to a power cable 1226, according to some embodiments. In some embodiments, power cable 1226 may connect a power pack 624 (see FIG. 6B) to the transducer case assembly 1250, thereby powering the transducer. In some embodiments, power cable 1226 may be a USB-A cable. Alternatively, in some embodiments, power cable 1226 may be any type of power cable, for example, but not limited to, micro-USB, USB-C, 8-pin, etc.

Figure 12C:
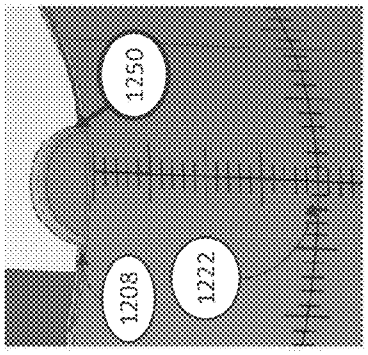
FIG. 12C shows a transducer case assembly inserted into a harness, according to some embodiments.

FIG. 12C shows a transducer case assembly inserted into a harness, according to some embodiments. As shown, the transducer case assembly may be placed inside the transducer securing portion 1208. The two-dimensional transducer securing portion scale 1222 may be used to align the transducer case assembly 1250 to the correct position.

Figure 12D:
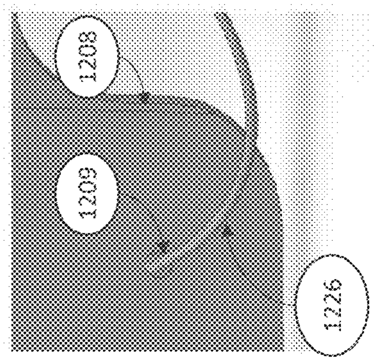
FIG. 12D shows a power cable with respect to a pocket of a harness for holding a transducer, according to some embodiments.

FIG. 12D shows a power cable 1226 with respect to a transducer securing portion 1208, according to some embodiments. Power cable 1226, which may connect power pack 924 (see FIG. 9B) to the transducer assembly 1250, may extend through transducer securing portion outlet 1209. In some embodiments, power pack 1124 may provide electric power to transducer case assembly 1250 via power cable 1226.

Figure 13:
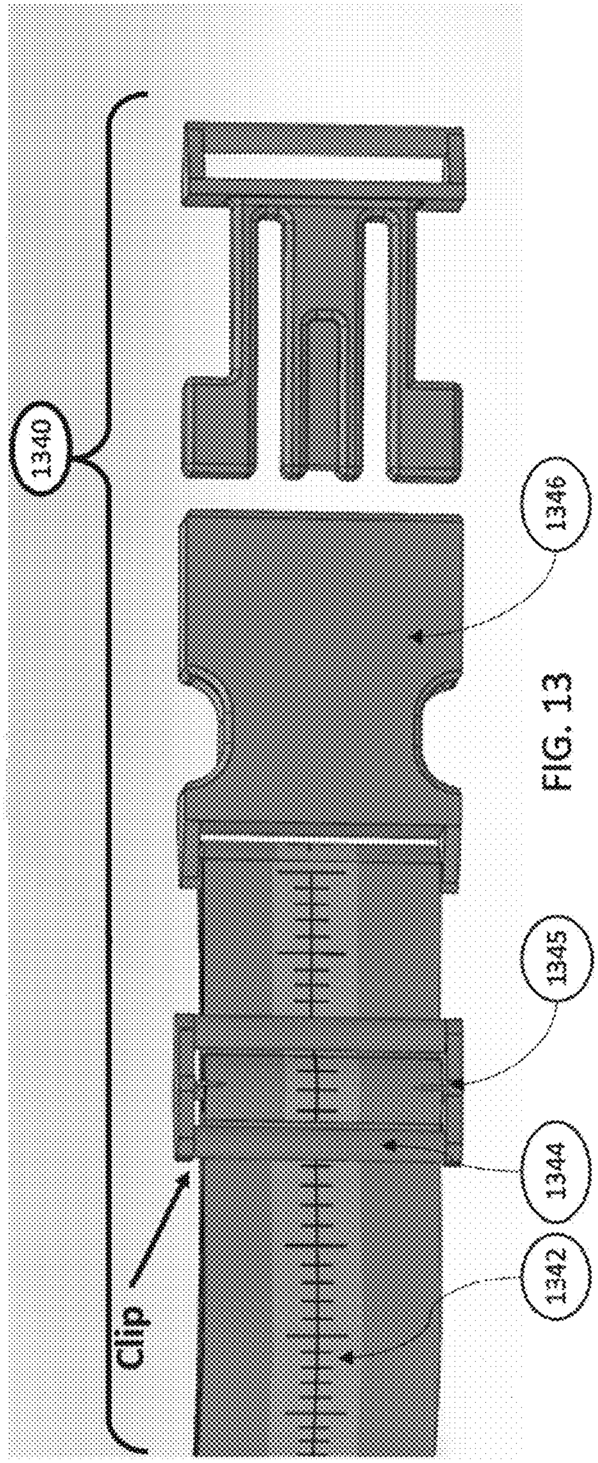
FIG. 13 shows a portion of an adjustable strap of a harness, according to some embodiments.

FIG. 13 shows a portion of an adjustable strap 1340 of a harness, according to some embodiments. As shown, adjustable strap 1340 can include scale 1342, clip 1344, and/or buckle 1346. In some embodiments, adjustable strap 1340 may be used for the adjustable waist strap of a harness described herein. In some embodiments, adjustable strap 1340 may be used to connect a rear panel of a harness to a shoulder strap and/or a front panel of a harness to a shoulder strap. Adjustable strap 1340 can include any features of adjustable waist strap 413 of FIG. 4B, 513 of FIG. 5, 613 of FIG. 6, 713 of FIG. 7, and or 1013 of FIG. 10.

As shown, scale 1342 includes a scale that extends lengthwise along the adjustable strap 1340. Scale 1342 can include any features of waist strap scale 410 of FIG. 4B, 610 of FIG. 6, and/or 1010 of FIG. 10, as well as any features of shoulder strap scales 520 of FIG. 5, 720 of FIG. 7, and/or 1020 of FIG. 10.

As shown, clip 1344 includes a clip that attaches to adjustable strap 1340 and holds the strap in place near the buckle 1346. Clip 1344 can include any features of waist strap clip 411 of FIG. 4B, 611 of FIG. 6, and/or 1011 of FIG. 10. In some embodiments, clip 1344 may include at least one clip pointer 1345.

As shown, clip pointer 1345 includes a thin pointer arm attached to clip 1344 that points towards scale 1342. In some embodiments, the clip pointer 1345 may extend partway through the middle of clip 1344 so that the clip pointer 1345 can align with line markers of the scale 1342. In some embodiments, the clip pointer 1345 can be used to read the scale 1342. In some embodiments, more than one clip pointer 1345 may be attached to clip 1344, such that the central axes of each pointer are parallel to the line markers of the scale 1342 and parallel to each other.

As shown, buckle 1346 includes a buckle that attaches the adjustable strap 1340 to another component of the harness. Buckle 1346 can include any features of waist strap buckle 412 of FIG. 4B, 612 of FIG. 6, and/or 1012 of FIG. 10, as well as any features of shoulder strap buckles 518 of FIG. 5, 718 of FIG. 7, and/or 1018 of FIG. 10.

Figure 17A:
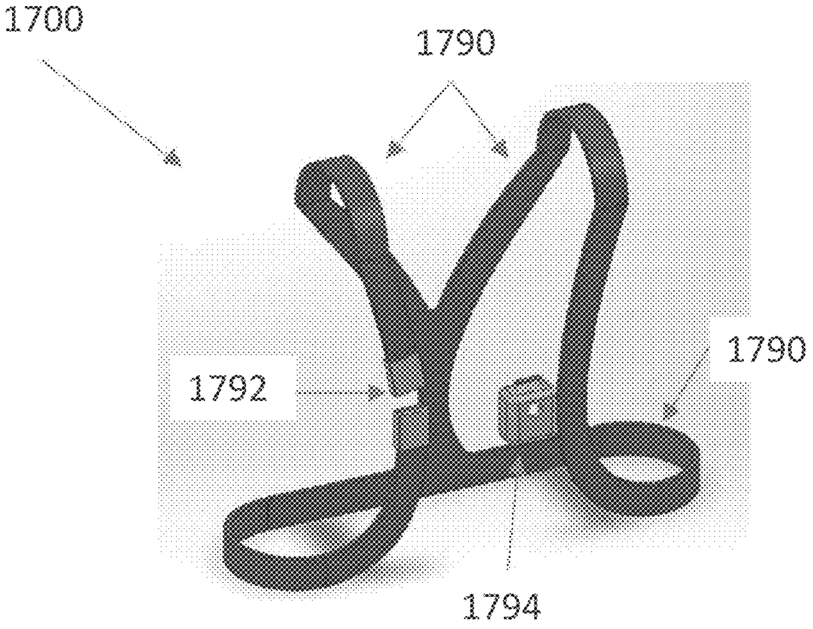
FIG. 17A is a diagram illustrating an example of a wearable harness/device, according to some embodiments.
Figure 17B:
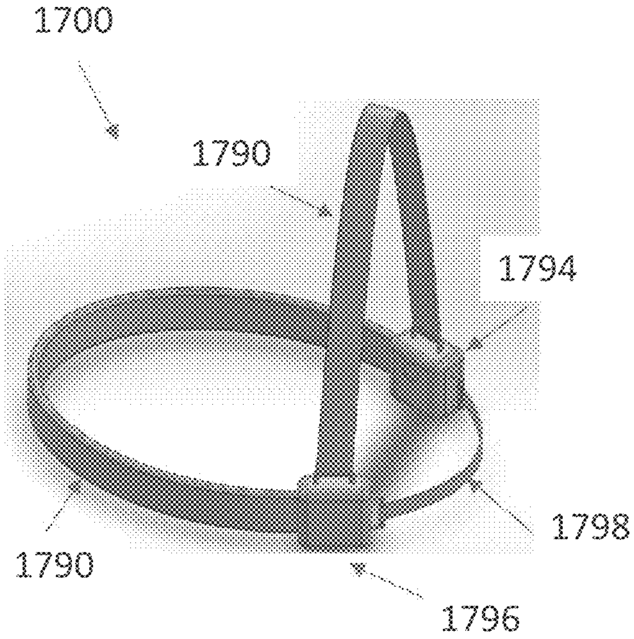
FIG. 17B is a diagram illustrating an example of a wearable harness/device, according to some embodiments.

FIGS. 17A, 17B, and 18A-G illustrate additional examples of a wearable harness according to some embodiments. Specifically, these figures show a wearable harness with the housing in the form of a body strap/garment/back brace or harness. In the examples shown in FIGS. 17A and 17B, the back brace 1700 includes straps 1790 that go over the subject's shoulders and around the subject's waist. A first component holder or housing 1794 is secured to the back brace 1700 and houses an ultrasound stimulation device that may be configured to target the spleen, as discussed further below. According to certain embodiments, the back brace 1700 may be adjusted to the subject. For example, the straps 1790 may be manually adjustable to allow the back brace 1700 to be fitted to the subject's size. In certain examples, the straps 1790 may be manually sized. In the example shown in FIG. 17A, a clip 1792 can be used to secure the back brace in place once the subject has put it on. In the example of FIG. 17A, the clip 1792 may be positioned to one side of the subject's chest for easy access by the subject. In the example of FIG. 17B, the back brace 1700 includes a second component holder 1796, and a connecting strap 1798 goes around the waist area and is attached to the housing 1794 and to the second component holder 1796. The second component holder 1796 is optional and may be used to house electronic components that may not fit within the housing 1794. In one example, the connecting strap 1798 may removably clip into (or be otherwise removably attached to) one or both of the housing components 1794 and the second component holder 1796 to allow the subject to easily put on and take off the back brace 1700. The housing 1794 may position the ultrasound stimulation device over the spleen.

FIGS. 18A-G illustrate another example of the wearable harness or device configured as a back brace 1800. In this example, the device includes a rigid central portion (also referred to as a back brace component) 1882 that extends horizontally along a portion of the subject's waist and vertically along a portion of the subject's back or spine. Flexible straps 1880 are attached to the rigid central portion and are configured to go over the subject's shoulders. The flexible straps 1880 may be made of neoprene or rubber, for example, and can be manually adjusted to fit the back brace to the subject. An ultrasound component holder 1884 is attached to the central rigid portion 1882 and houses an ultrasound stimulation device 188 The material and rigidity of the back brace component 1882 may make it comfortable while wearing and reliable to position the ultrasound component holder 1884 such that the ultrasound stimulation device 1800 always targets the spleen. In one embodiment, the back brace component 1882 has triple layered material, the middle being soft and expandable.

Figure 18A:
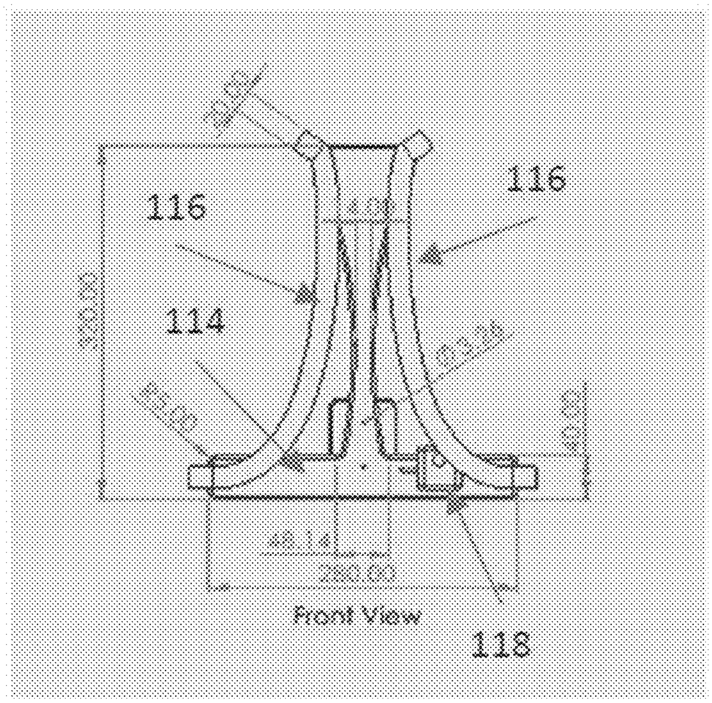
FIG. 18A is a diagram showing an example of a wearable harness/device, according to some embodiments.
Figure 18B:
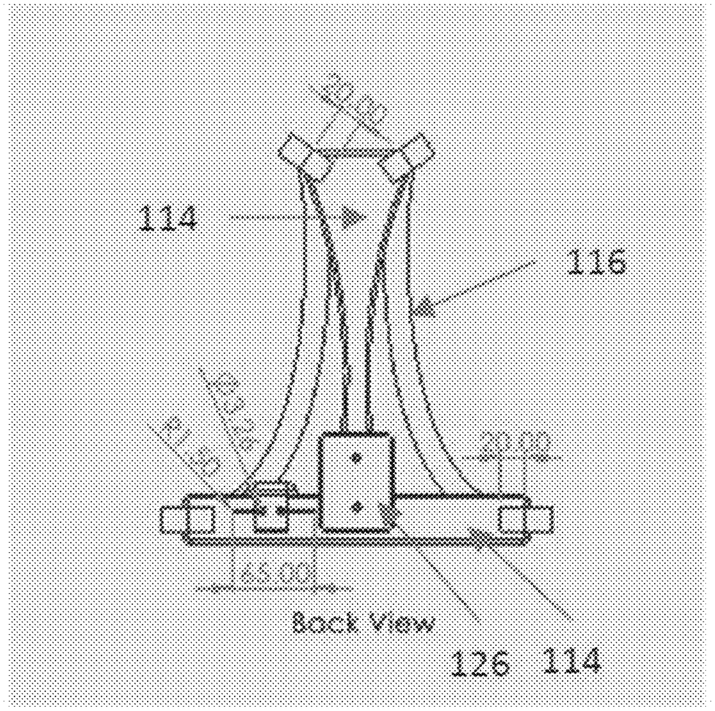
FIG. 18B is a diagram showing an example of a wearable harness/device, according to some embodiments.
Figure 18C:
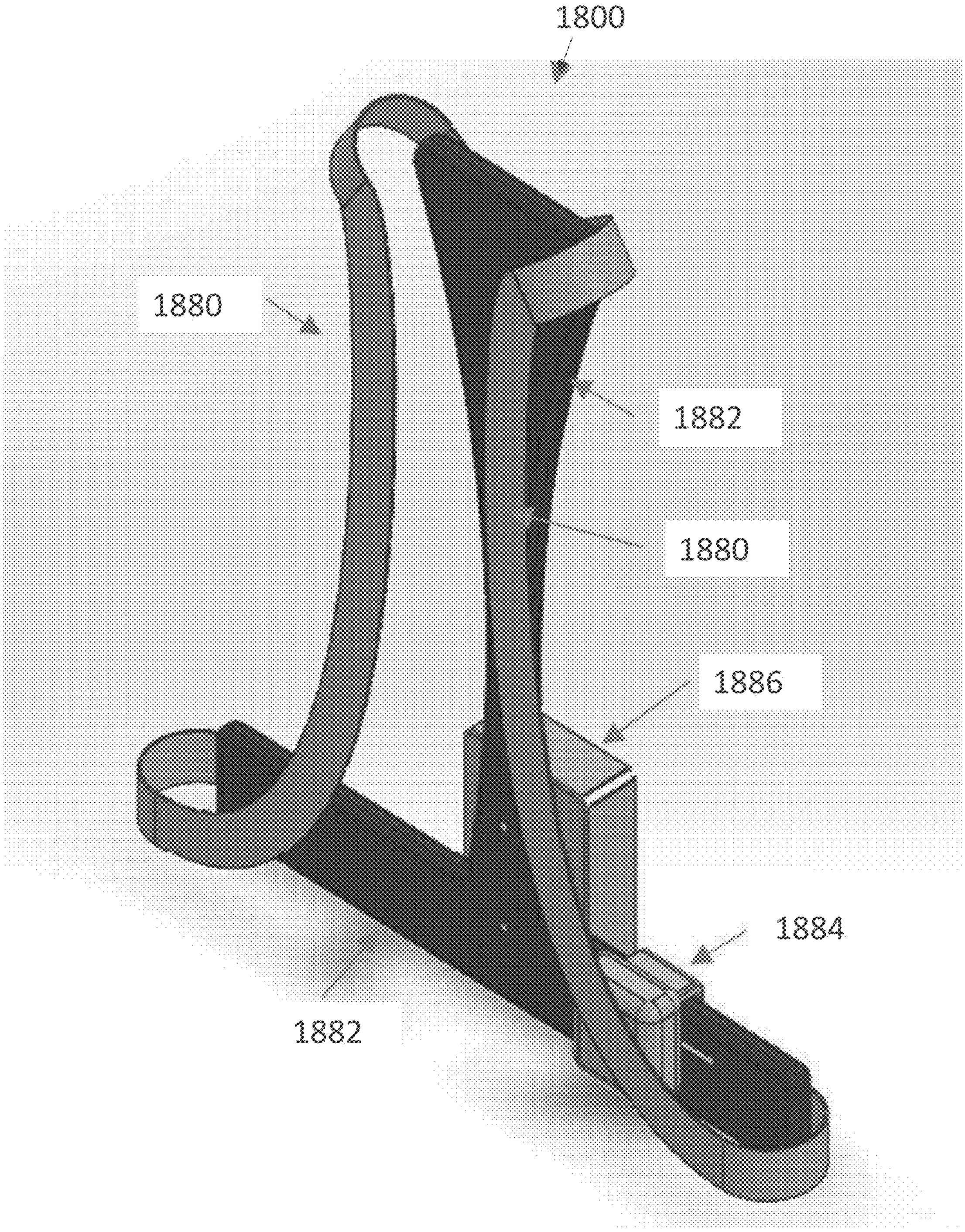
FIG. 18C is a diagram showing an example of a wearable harness/device, according to some embodiments.
Figure 18D:
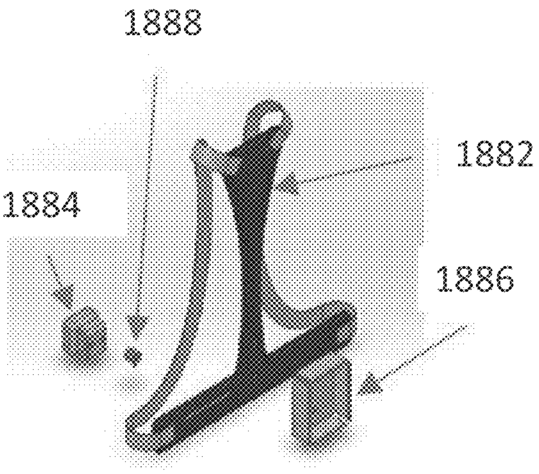
FIG. 18D is a partially exploded view of a portion of the wearable harness/device of FIG. 18C, according to some embodiments.
Figure 18E:
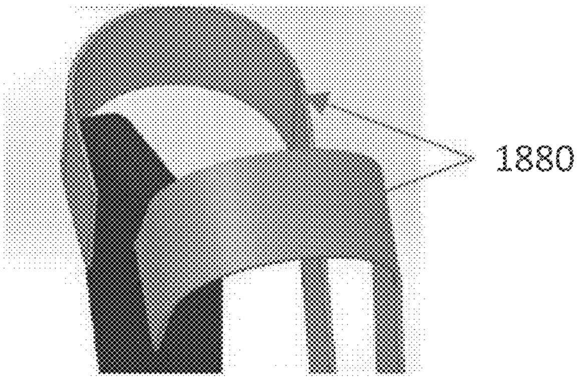
FIG. 18E is an enlarged view of a portion of the wearable harness/device of FIG. 18C, according to some embodiments.
Figure 18F:
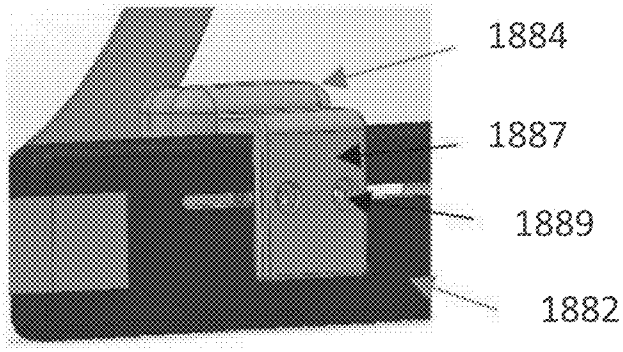
FIG. 18F is an enlarged view of a portion of the wearable harness/device of FIG. 18C, according to some embodiments.
Figure 18G:
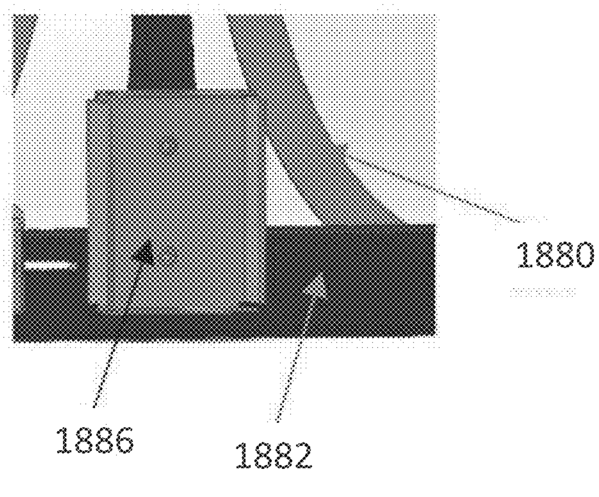
FIG. 18G is an enlarged view of a portion of the wearable harness/device of FIG. 18C, according to some embodiments.

Referring to FIG. 18F, in certain examples, the ultrasound component holder 1884 may include a clip or clamp portion 1887, for easy personalized adjustment to every subject, that is configured to fit over the back brace component 1882 to secure the ultrasound component holder 1884 to the back brace component 1882 by friction. In certain examples, the clip portion 1887 may include one or more holes 1889 to accommodate fasteners to secure the ultrasound component holder 1884 to the back brace 1882. FIGS. 18A and 18B show some examples of dimensions of the wearable harness; however, it is to be appreciated that these dimensions are provided as one example only, and various embodiments of the wearable harness or device may have different dimensions and configurations, not limited to the specifics illustrated in FIGS. 18A and 18B.

As shown in FIGS. 18A-D and 18G, in certain embodiments, the wearable harness (i.e., wearable device) may further include an additional component holder 1886 attached to the back brace component 1882. The additional component holder 1886 may be attached to the back brace component 1882 using one or more fasteners, such as screws, for example. An electronic component housed within the additional component holder 1886 may be connected to the ultrasound stimulation device, either wirelessly, or via wires that travel along the back brace component 1882. The additional component holder 1886 is optional and may accommodate any other electronic hardware that may be used in certain examples for either biomarker monitoring, storing data, wireless communications, or other applications.

Methods according to certain embodiments comprise the use of ultrasound waves in the low-intensity or low frequency range applied non-invasively to nerves, specifically the splenic nerve, and nerves surrounding the spleen to modulate, either inhibit or activate, the immune response. The ultrasound stimulation device may include one or several components that are commercially available or custom-made and generate the ultrasound waves, such as ultrasound emitters, transducers, piezo-electric transducers, composite transducers, capacitive micromachined ultrasound transducer or any other ultrasound emitting transducers, that could be single or multiple transducers and the waves could be in any shape both being focused and unfocused depending on the desired outcome that is needed. In certain examples, the ultrasound pressure ranges from 10 kPa to 800 kPa. The focused ultrasound may be emitted from a shallow ultrasound-focusing cone. In one embodiment, the ultrasound frequency exhibited to the body is <2.5 MHz. In certain examples, the ultrasound frequency may be in the range from 500 kHz to 2.5 MHz, with a pulse repetition ranging from 0.1 to 10 milliseconds (ms). The pulse length may range from 100 to 300 microseconds.

According to certain implementations, subjects may undergo treatment for from 1 minute to 30 minutes per day, for example, from 5 to 30 minutes per day, or from 10 to 15 minutes per day. The number of days of treatment may be determined by the subject's doctor, and may be up to the full lifetime of the subject. The number of days of treatment, and frequency of the treatment, may depend on health condition and disease state of the subject, and can range from daily to weekly to monthly.

Kidney transplant subjects can use the wearable device or harness according to various embodiments to deliver ultrasound stimulation to their spleens and reduce their cytokine levels, in addition to or instead of the cocktail of immunosuppressants which are currently the standard of care for subjects who have undergone a kidney transplantation. For kidney treatment, the ultrasound may be focused on the splenic region of the abdomen, as discussed above. However, in other applications, the ultrasound may be focused at different bodily regions, as appropriate.

Thus, aspects and embodiments provide a wearable harness for an ultrasound-emitting device that can be used to provide targeted ultrasound stimulation to one or more organs in a subject's body. For example, the wearable harness can be used with an ultrasound transducer that is applied non-invasively to the spleen. As discussed above, the wearable device/harness can be implemented in a form that is comfortable for the subject to wear and configured to be easy for the subject to correctly position the ultrasound emitter without requiring detailed knowledge of the organ location within the subject's body. The wearable device or harness can be used by the subject at home, without requiring the presence of a physician or another trained medical professional. Ultrasound stimulation/modulation provided by the ultrasound device of the harness may advantageously treat or improve a variety of medical conditions, as discussed above, including (but not limited to) reducing kidney transplant rejection through ultrasound applied to the spleen. Furthermore, as discussed above, embodiments of the device can be used to stimulate the splenic nerve and other nerves surrounding it to modulate other bodily functions beyond dampening the immune system in organ transplants. For example, Alzheimer's disease (e.g., remyelination induction of the nerves), traumatic brain injury, chronic traumatic encephalopathy, autoimmune diseases such as lupus, dermatitis, eczema, psoriasis, psoriatic arthritis, endometriosis, scleroderma, Sjogren's, fibromyalgia, neuropathy, Wegener's granulomatosis, vascultities, temporal arteritis, celiac's disease, Crohn's disease, eczema, ulcerative colitis, inflammatory bowel disease, rheumatoid arthritis, osteoarthritis, ankylosing spondylitis, non-alcoholic fatty liver disease, alcoholic fatty liver disease, dilated cardiomyopathy, hypertrophic cardiomyopathy, restrictive cardiomyopathy, myocardial infarction, coronary artery disease, cardiovascular disease, reperfusion injury, diabetes types I and II, multiple sclerosis, depression, schizophrenia, bipolar disorder, autism spectrum disorder, major depression disorder, post-traumatic stress disorder, skin cancer, cellulitis, vitiligo, rosacea, cervicitis, herpes, HIV, menopause, aging, hair loss, hair greying, pelvic inflammatory disease, endometriosis, infertility, antiphospholipid syndrome, post and pre-transfusions, Rh incompatibility during pregnancy, post-plastic surgery, post-surgical interventions, sleep disorders, circadian rhythm disorders, insomnia, jet lag, hepatitis, and obesity.

Figure 19:
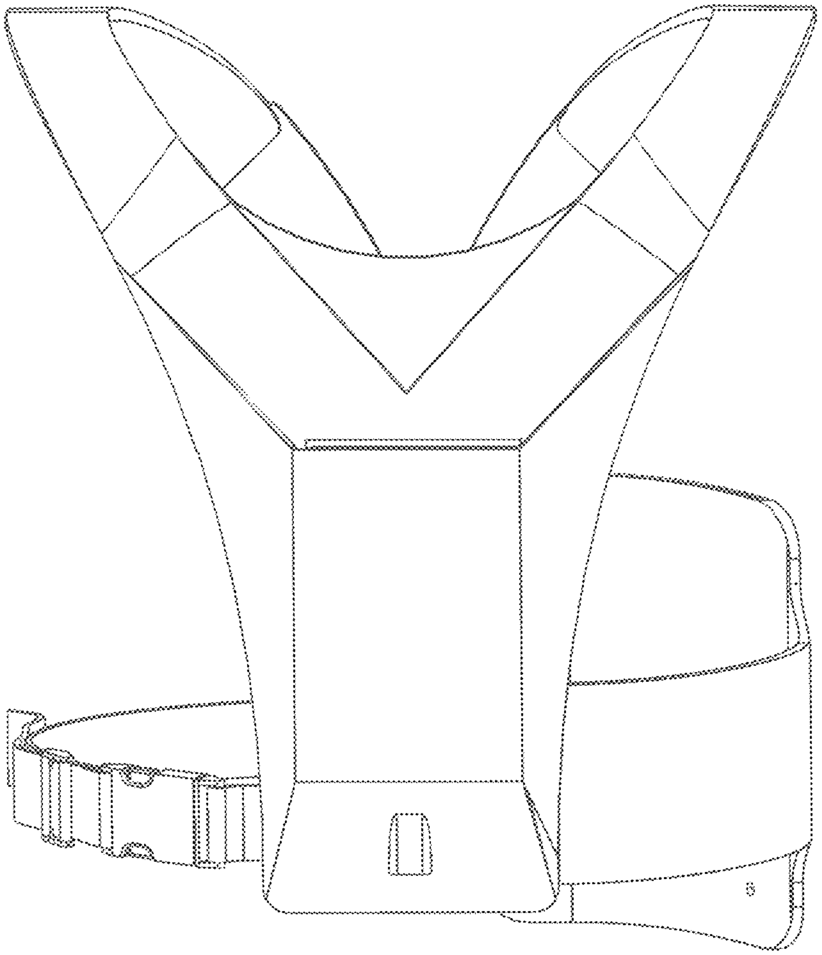
FIG. 19 is a line drawing of a front of a wearable harness, such as that depicted in FIG. 6 and according to some embodiments.
Figure 20:
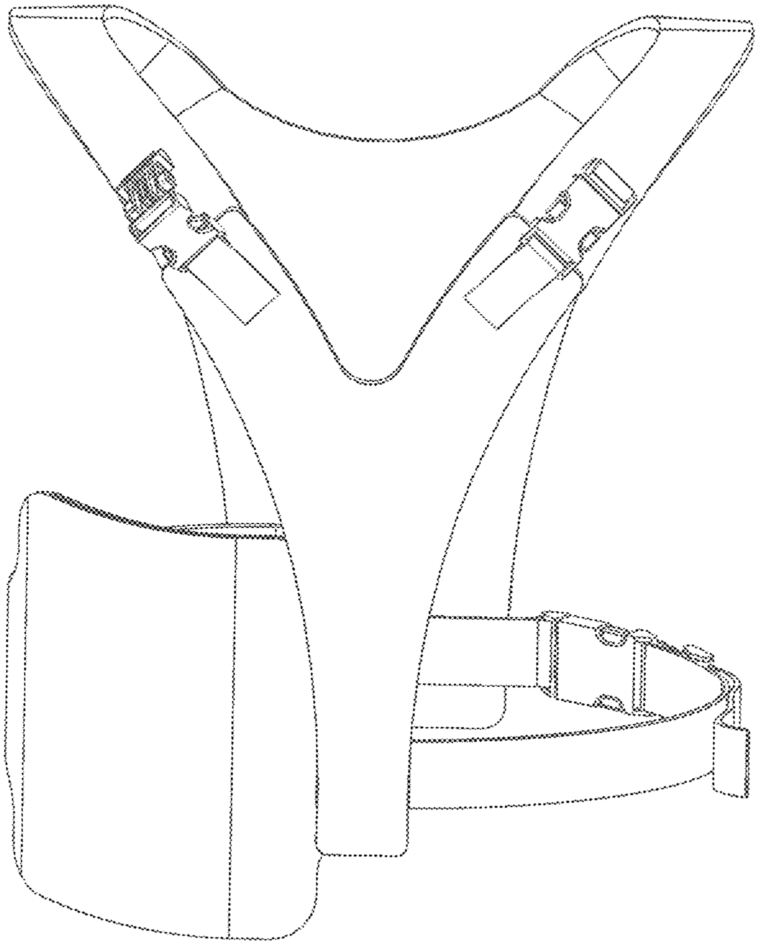
FIG. 20 is a line drawing of a rear of a wearable harness, such as that depicted in FIG. 7 and according to some embodiments.
Figure 21:
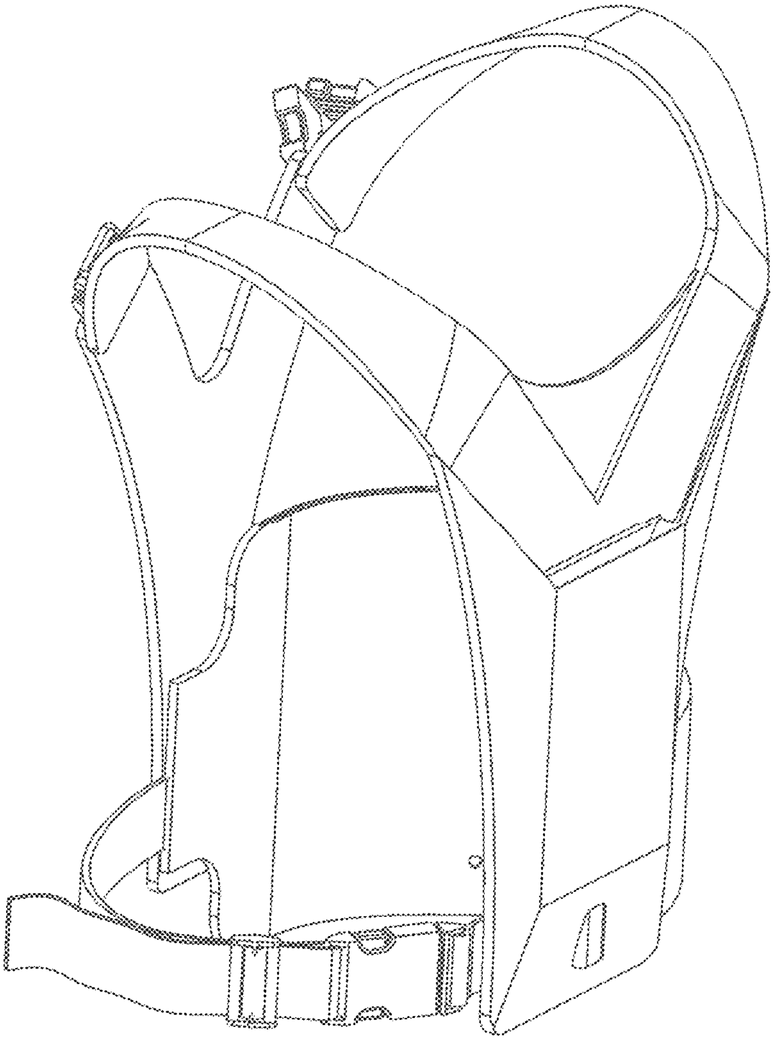
FIG. 21 is a perspective view of a wearable harness, according to some embodiments.
Figure 22:
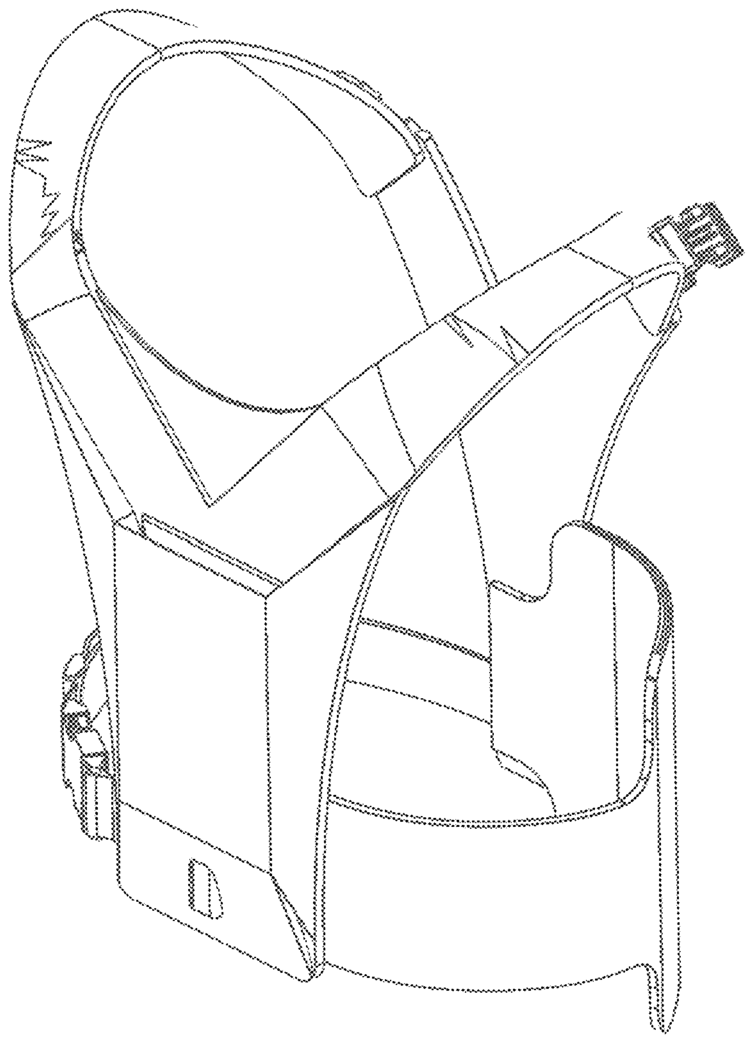
FIG. 22 is a perspective view of a wearable harness, according to some embodiments.
Figure 23:
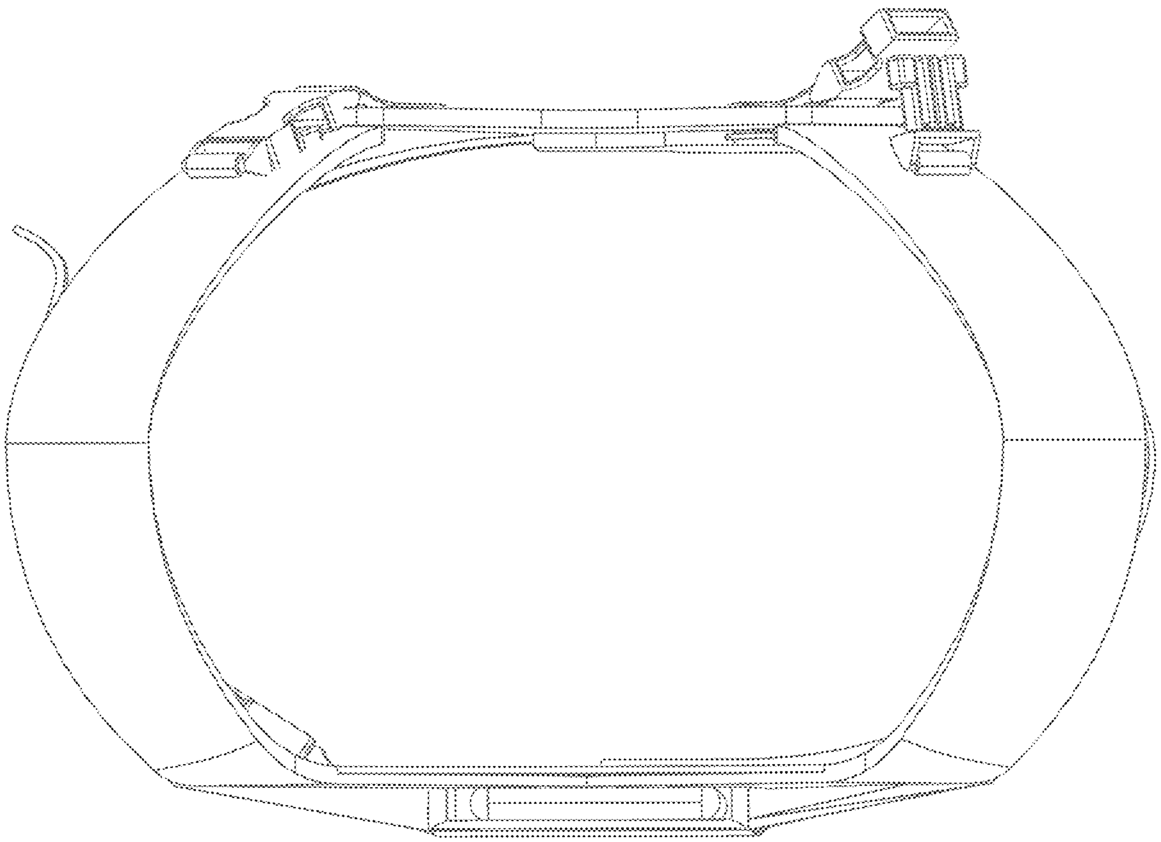
FIG. 23 is a line drawing of a top of a wearable harness, such as that depicted in FIG. 9A and according to some embodiments.
Figure 24:
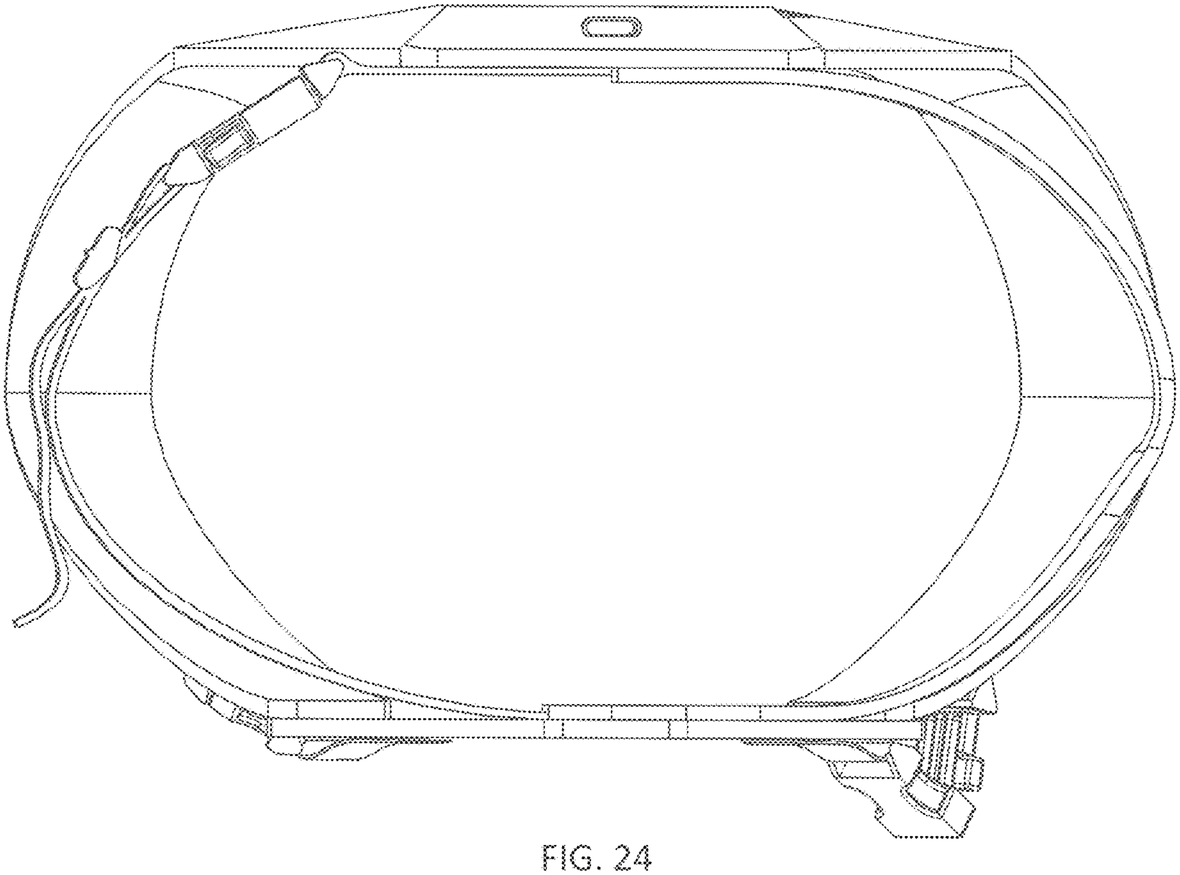
FIG. 24 is a line drawing of a bottom of a wearable harness, such as that depicted in FIG. 9B and according to some embodiments.

FIG. 19 is a line drawing of a front of a wearable harness, such as that depicted in FIG. 6 and according to some embodiments. FIG. 20 is a line drawing of a rear of a wearable harness, such as that depicted in FIG. 7 and according to some embodiments. FIG. 21 is a perspective view of a wearable harness, according to some embodiments. FIG. 22 is a perspective view of a wearable harness, according to some embodiments. FIG. 23 is a line drawing of a top of a wearable harness, such as that depicted in FIG. 9A and according to some embodiments. FIG. 24 is a line drawing of a bottom of a wearable harness, such as that depicted in FIG. 9B and according to some embodiments.

Treatment Unit

In some embodiments, a treatment unit may comprise an ultrasound transducer only. In some embodiments, a treatment unit may comprise an ultrasound transducer and a mechanical lens.

Figure 14A:
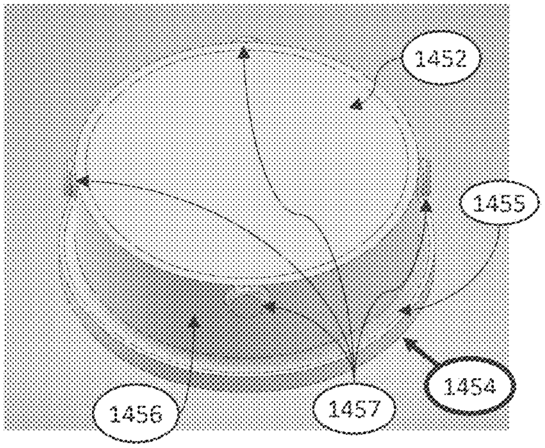
FIG. 14A shows a transducer inside of a transducer case, according to some embodiments.

FIG. 14A shows a transducer 1452 inside of a transducer case 1454, according to some embodiments. As shown, transducer case 1454 may include a case base 1455, a case sidewall 1456, and a plurality of protrusions 1457. In some embodiments, the case base 1455 may be circular in shape. In some embodiments, the plurality of protrusions 1457 may be located evenly spaced along the case sidewall 1456. In some embodiments, the plurality of protrusions 1457 may be positioned along the case sidewall 1456 such that they are proximate to the case base 1455 of the transducer case 1454. In some embodiments, the plurality of protrusions 1457 may be positioned along the case sidewall 1456 at an edge at which the case sidewall 1456 meets the case base 1455. In some embodiments, transducer 1452 may be placed within the transducer case 1454 so that at least a portion of the outer surface of the transducer 1452 is flush with the inner surface of the case sidewall 1456. In some embodiments, the transducer case 1454 may be 3D-printed. In some embodiments, at least a portion of the exterior of the transducer case 1454 may be coated with a fastening material, such as VELCRO®, to secure the transducer case 1454 to the interior of a transducer securing portion, which may be lined with the same fastening material.

Figure 14B:
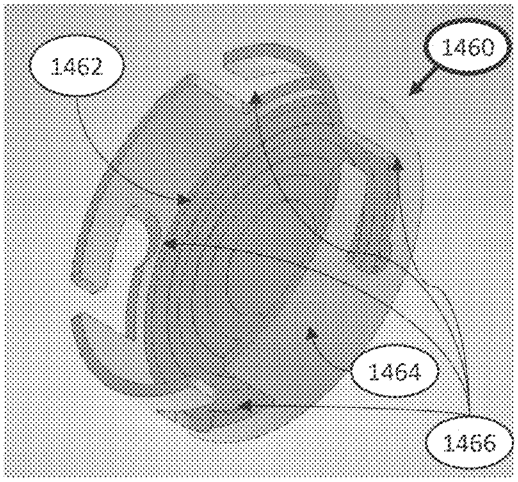
FIG. 14B shows an interchangeable mechanical lens, according to some embodiments.

FIG. 14B shows an interchangeable mechanical lens 1460, according to some embodiments. As shown, interchangeable mechanical lens 1460 includes a mechanical lens face 1462, a lens sidewall 1464, and a plurality of notches 1466. In some embodiments, the interchangeable mechanical lens 1460 may be positioned between the transducer 1452 and the subject and configured such that it may adjust ultrasonic waves emitted by the transducer 1452. In some embodiments, the mechanical lens face 1462 may be a flat Fresnel lens. In some embodiments, the mechanical lens face 1462 may be circular in shape. In some embodiments, the mechanical lens face 1462 may include variations in thickness such that one surface of the lens is flat and another surface of the lens is ridged. For example, the mechanical lens face 1462 may include concentric circular rings of different thicknesses centered around the central axis of the mechanical lens face 1462. As shown, the lens sidewall 1464 may include a plurality of notches 1466 configured to receive one or more protrusions 1457 of a transducer case 1454. In some embodiments, interchangeable mechanical lens 1460 may be mounted over the transducer case 1454 so that at least a portion of the outer surface of the transducer case 1454 is flush with the inner surface of the lens sidewall 1464. In some embodiments, the plurality of notches 1466 may be positioned along the lens sidewall 1464 such that they are proximate to the edge of the lens sidewall 1464 that is farthest from the mechanical lens face 1462. In some embodiments, one or more of the plurality of notches 1466 may have an L-shape, such that a line drawn through the center of a notch may extend vertically toward the mechanical lens face 1462, then horizontally along the case sidewall 1464. In some embodiments, the interchangeable mechanical lens 1460 may be oriented such that a flat surface of mechanical lens face 1462 faces toward the subject. In such embodiments, ultrasonic waves emitted by transducer 1452 may be focused by the interchangeable mechanical lens 1460 and directed into the subject's body. In some embodiments, the interchangeable mechanical lens 1460 may be 3D-printed separately from the transducer case 1454 such that lenses of different focal distances can be interchangeably used with the same transducer case 1454. Alternatively, in some embodiments, the mechanical lens 1460 may be 3D-printed together with the transducer case 1454 such that the lens is not interchangeable.

Figure 14C:
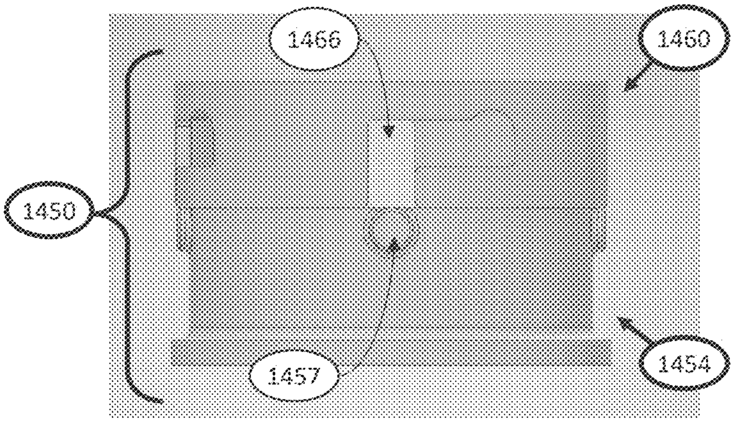
FIG. 14C shows a transducer case assembly, according to some embodiments.

FIG. 14C shows a transducer case assembly 1450, according to some embodiments. As shown, transducer case assembly 1450 includes an interchangeable mechanical lens 1460 mounted over a transducer case 1454. In some embodiments, the lens sidewall 1464 may include a plurality of notches 1466 configured to receive one or more protrusions 1457 of a transducer case 1454. In some embodiments, one or more of the plurality of notches 1466 may have an L-shape, such that a line drawn through the center of a notch may extend vertically toward the mechanical lens face 1462, then horizontally along the case sidewall 1464. In some embodiments, to mount the interchangeable mechanical lens 1460 over the transducer case 1454, the interchangeable mechanical lens 1460 may be positioned so that one or more of its plurality of notches 1466 may align vertically with one or more of the plurality of protrusions 1457 on the transducer case 1454. The interchangeable mechanical lens 1460 is then twisted horizontally so that the plurality of protrusions 1457 lock into the plurality of notches 1466, thereby fastening the interchangeable mechanical lens 1460 and the transducer case 1454 together.

Figure 15:
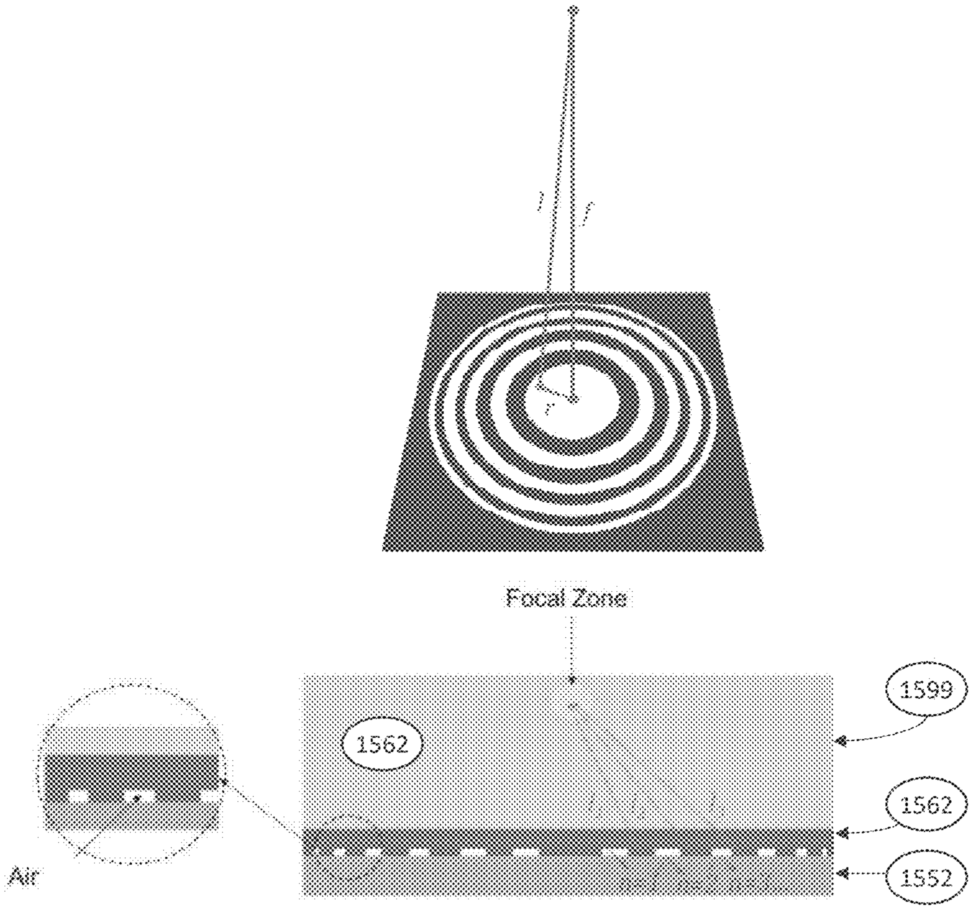
FIG. 15 shows a mechanical lens face and transducer with respect to a subject, according to some embodiments.

FIG. 15 shows a mechanical lens face 1562 and transducer 1552 with respect to a patient 1599, according to some embodiments. In some embodiments, the mechanical lens face 1562 may be a flat Fresnel lens. The material of the mechanical lens face 1562 may be a 3D-printable plastic, for example, but not limited to, polystyrene, ABS, PLA, nylon, etc. In some embodiments, the mechanical lens face 1562 may include variations in thickness such that one surface of the lens is flat and another surface of the lens is ridged. For example, the mechanical lens face 1562 may include concentric circular rings of different thicknesses centered around the central axis of a circular mechanical lens face 1562. In such embodiments, the flat surface of the mechanical lens face 1562 may face toward the patient 1599. In such embodiments, ultrasonic waves emitted by transducer 1552 may be focused through the mechanical lens face 1562 and directed into the patient's body. The mechanical lens face 1562 can focus ultrasonic waves because ultrasonic waves travel at different speeds through materials of different density. As shown, in the prior embodiment, if a transducer 1552 were to emit ultrasonic waves toward the patient 1599, the waves would first pass through two materials of different densities: the 3D-printable plastic of the mechanical lens face 1562, and the air trapped between the rings of the mechanical lens face 1562 and the surface of the transducer 1552. The thicknesses of these rings are mathematically selected to allow waves with certain wave phases to constructively interfere and pass through the mechanical lens face 1562 into the desired focal zone. For constructive interference, the difference in phase between waves from a given ring are less than half a wavelength, meaning $l-f<\lambda/4$. By writing $l^2=r^2+f^2$, we get $$r_n^2 = n\lambda\left(f + \frac{n\lambda}{4}\right),$$

in which f=focal distance as measured from the central axis of the mechanical lens face 1562, λ=wavelength, r=radius, and n=number of rings. Note that by increasing the number of rings, it is possible to achieve greater precision in focusing ultrasonic waves toward a target focal distance. By changing the number and radii of the rings, it is also possible to produce mechanical lens faces 1562 with different focal distances.

Figure 16A:
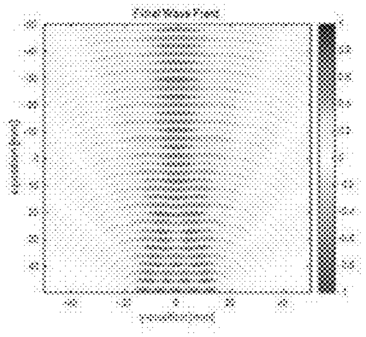
FIG. 16A shows a two-dimensional final wave field simulation of ultrasound transmission without a lens, according to some embodiments.
Figure 16B:
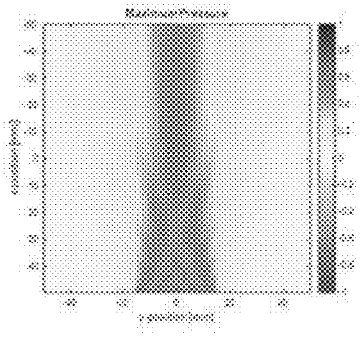
FIG. 16B shows a two-dimensional maximum pressure simulation of ultrasound transmission without a lens, according to some embodiments.
Figure 16C:
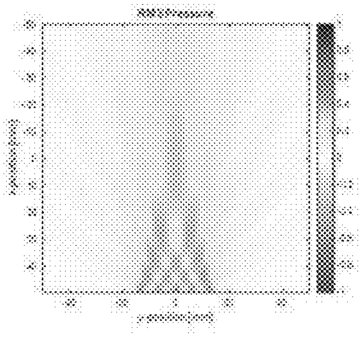
FIG. 16C shows a two-dimensional root-mean-square (hereafter, "RMS") pressure simulation of ultrasound transmission without a lens, according to some embodiments.
Figure 16D:
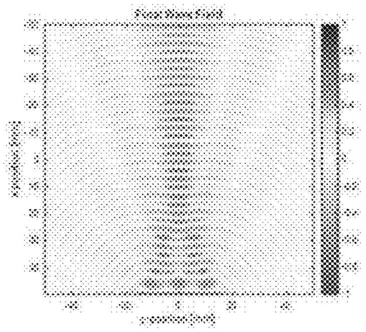
FIG. 16D shows a two-dimensional final wave field simulation of ultrasound transmission with a 20 mm focal distance mechanical lens, according to some embodiments.
Figure 16E:
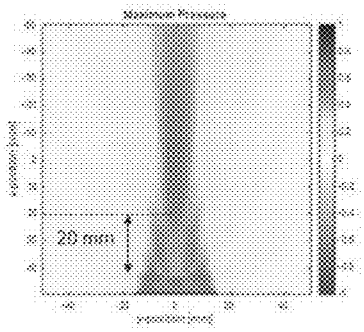
FIG. 16E shows a two-dimensional maximum pressure simulation of ultrasound transmission with a 20 mm focal distance mechanical lens, according to some embodiments.
Figure 16F:
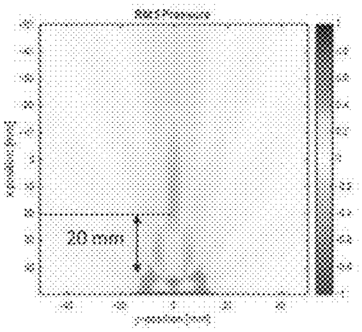
FIG. 16F shows a two-dimensional RMS pressure simulation of ultrasound transmission with a 20 mm focal distance mechanical lens, according to some embodiments.

Example of Simulated Results of Ultrasound Transmission Through Human Tissue, with and without a 20 mm Focal Distance Mechanical Lens FIGS. 16A-F show various simulations of how ultrasonic waves may pass through a medium—in this example, human tissue—and interact differently with the medium depending on whether mechanical lens is used to focus the ultrasonic waves. In these simulations, simulated ultrasonic waves emitted by a transducer were focused through a simulated mechanical lens and directed into simulated human tissue representing a subject's body. FIGS. 16A-C show simulations of ultrasound transmission without a lens; FIGS. 16D-F show the same simulations but with a 20 mm focal distance mechanical lens. Note that by changing the number and radii of the rings, it is possible to produce mechanical lenses with focal distances other than 20 mm. In some embodiments, the focal distances may range between 0.2-20 cm. In some embodiments, the focal distance of a lens may be less than or equal to 20, 15, 10, 5, 1 or 0.5 cm. In some embodiments, the focal distance of a lens may be greater than or equal to 0.2, 0.5, 1, 5, 10, or 15 cm.

FIG. 16A shows a two-dimensional final wave field simulation of ultrasound transmission without a lens, according to some embodiments. FIG. 16D shows a two-dimensional final wave field simulation of ultrasound transmission with a 20 mm focal distance mechanical lens, according to some embodiments. These two wave field simulations, FIGS. 16A and 16D, show how the field pattern of ultrasonic waves may be modulated by passing through a mechanical lens. FIG. 16D shows a narrower overall field pattern than FIG. 16A, especially at the 20 mm distance mark, indicating that the mechanical lens may be successful at focusing ultrasonic waves at a target 20 mm beneath a subject's skin.

FIG. 16B shows a two-dimensional maximum pressure simulation of ultrasound transmission without a lens, according to some embodiments. FIG. 16E shows a two-dimensional maximum pressure simulation of ultrasound transmission with a 20 mm focal distance mechanical lens, according to some embodiments. These two maximum pressure simulations, FIGS. 16B and 16E, show how ultrasonic waves may be modulated by passing through a mechanical lens. Compared to FIG. 16B which does not use a lens, FIG. 16E shows a narrower area of pressure at the 20 mm distance mark, indicating that ultrasonic waves are more focused at that distance. This indicates that the mechanical lens may be successful at focusing ultrasonic waves at a target 20 mm beneath a subject's skin.

FIG. 16C shows a two-dimensional RMS pressure simulation of ultrasound transmission without a lens, according to some embodiments. FIG. 16F shows a two-dimensional RMS pressure simulation of ultrasound transmission with a 20 mm focal distance mechanical lens, according to some embodiments. These two RMS pressure simulations, FIGS. 16C and 16F, show how the intensity of ultrasonic waves may be modulated by passing through a mechanical lens. Compared to FIG. 16C which does not use a lens, FIG. 16F shows a narrower area of intensity at the 20 mm distance mark, indicating that ultrasonic waves are more focused at that distance. This indicates that the mechanical lens may be successful at focusing ultrasonic waves at a target 20 mm beneath a subject's skin.

ENUMERATED EMBODIMENTS

The following enumerated embodiments are representative of some aspects of the invention.

1. A wearable ultrasound stimulation device configured to be worn by a patient in need thereof and comprising:
   a wearable housing; and
   an ultrasound stimulation module accommodated by the wearable housing and configured to emit ultrasonic stimulation pulses toward a target region of the body of the patient.
2. The wearable ultrasound stimulation device of embodiment 1 wherein the wearable housing is a belt configured to be worn around the chest of the patient.
3. The wearable ultrasound stimulation device of embodiment 1 wherein the wearable housing is a patch configured to be adhered to the back of the patient covering an area of the spleen.
4. The wearable ultrasound stimulation device of embodiment 1 wherein the wearable housing is a harness configured to the worn around the shoulders and waist of the patient.
5. The wearable ultrasound stimulation device of embodiment 4 wherein the harness includes:
   a rigid back brace component;
   a pair of shoulder straps attached to the rigid back brace component; and
   an ultrasound component holder attached to the rigid back brace component, the ultrasound stimulation module being housed within the ultrasound component holder.
6. The wearable ultrasound stimulation device of embodiment 5 wherein the ultrasound component holder includes a clip portion configured to fit over a portion of the rigid back brace component to frictionally secure the ultrasound component holder to the rigid back brace component.
7. The wearable ultrasound stimulation device of embodiment 5 wherein the shoulder straps are made of neoprene, rubber, or a flexible smart material.
8. The wearable ultrasound stimulation device of embodiment 5 further comprising an additional component holder attached to the rigid back brace component.
9. The wearable ultrasound stimulation device of any one of embodiments 1-8 wherein the target region is the spleen.
10. A system for securing an ultrasound transducer over a spleen of a subject, the system comprising:
    - a harness comprising:
      - a front portion configured to hold a power pack;
      - a rear portion connected to the front portion by a first shoulder strap and a second shoulder strap;
      - an adjustable waist strap configured to wrap around a subject's waist and connect the front portion and the rear portion; and
      - a transducer securing portion located on the adjustable waist strap and configured to be positioned over a spleen of a subject, wherein the transducer securing portion comprises a two-dimensional scale; and
    - a treatment unit comprising:
      - an ultrasound transducer configured to couple to the transducer securing portion of the harness; and
      - a mechanical lens positioned between the ultrasound transducer and the subject, the mechanical lens comprising a plurality of concentric rings and configured to adjust ultrasonic waves emitted by the ultrasound transducer.

11. The system of embodiment 10, wherein the transducer securing portion receives and secures an ultrasound transducer with a mechanism comprising a pop-lock, a magnet, VELCRO®, locking pins, clips, or a key-in arms mechanism.
12. The system of embodiment 10 or 11, wherein a connection region between the first shoulder strap and the rear portion and a connection region between the second shoulder strap and the rear portion comprise an adjustable clasp.
13. The system of any of embodiments 10-12, wherein the adjustable clasp is configured to connect and disconnect and adjust a connection position between the rear portion and the first shoulder strap or the rear portion and the second shoulder strap.
14. The system of any of embodiments 10-13, wherein the connection position comprises an overlap region between the first shoulder strap and the rear portion or the second shoulder strap and the rear portion.
15. The system of any of embodiments 10-14, wherein the connection position comprises no overlap region between the first shoulder strap and the rear portion or the second shoulder strap and the rear portion.
16. The system of any of embodiments 10-15, wherein the front portion is configured to be positioned over the subject's chest.
17. The system of any of embodiments 10-16, wherein the rear portion is configured to be positioned over the subject's back.
18. The system of any of embodiments 10-17, wherein the power pack is connected to the ultrasound transducer with a power cable.
19. The system of any of embodiments 10-18, wherein the mechanical lens is configured to adjust ultrasonic waves emitted by the ultrasound transducer to a specific focal distance.
20. The system of embodiment 19, wherein the focal distance is 0.2-20 cm
21. A harness for positioning an ultrasound transducer to a subject, the harness comprising:
    - a front portion configured to hold a power pack;
    - a rear portion connected to the front portion by a first shoulder strap and a second shoulder strap;
    - an adjustable waist strap configured to wrap around a subject's waist and connect the front portion and the rear portion; and
    - a transducer securing portion located on the adjustable waist strap and configured to be positioned over a spleen of a subject, wherein the transducer securing portion comprises a two-dimensional scale.
22. The harness of embodiment 21, wherein the transducer securing portion is configured to receive a treatment unit such that the harness positions the treatment unit over the spleen of the subject.
23. The harness of embodiment 22, wherein the treatment unit comprises an ultrasound transducer.
24. The harness of embodiment 22 or 23, wherein the treatment unit comprises a mechanical lens comprising a plurality of concentric rings and configured to adjust ultrasonic waves emitted by the ultrasound transducer.
25. A treatment unit comprising:
    - an ultrasound transducer; and
    - a mechanical lens comprising a plurality of concentric rings and configured to adjust ultrasonic waves emitted by the ultrasound transducer.
26. The treatment unit of embodiment 25, wherein the mechanical lens is configured to adjust ultrasonic waves emitted by the ultrasound transducer to a specific focal distance.
27. The treatment unit of embodiment 25 or 26, wherein the focal distance is 1-3 cm.
28. A system for securing an ultrasound transducer over a spleen of a subject, the system comprising:
    - a harness comprising:
        - a front portion configured to hold a power pack;
        - a rear portion connected to the front portion by a first shoulder strap and a second shoulder strap;
        - an adjustable waist strap configured to wrap around a subject's waist and connect the front portion and the rear portion; and
        - a transducer securing portion located on the adjustable waist strap and configured to be positioned over a spleen of a subject, wherein the transducer securing portion comprises a two-dimensional scale, and
    - an ultrasound transducer configured to couple to the transducer securing portion of the harness.
29. A harness for positioning an ultrasound transducer to a subject, the harness comprising:
    - a transducer securing portion configured to receive an ultrasound transducer and secure the ultrasound transducer in a first location directly over a spleen of a subject.
30. The harness of embodiment 29, wherein the transducer securing portion comprises a two-dimensional scale for guiding the subject to reposition the ultrasound transducer in a second location identical to the first location.
31. A method of using a harness for positioning an ultrasound transducer to a subject, the method comprising:
    - securing a treatment unit to a transducer securing portion of a harness;
    - placing the harness on a subject such that the treatment unit is positioned over a spleen of the subject.
32. The method of embodiment 31, wherein securing a treatment unit to a transducer securing portion of a harness comprises positioning the treatment unit to the transducer securing portion with the guidance of a two-dimensional scale on the transducer securing portion.
33. The method of embodiment 31 or 32, wherein securing a treatment unit to a transducer securing portion of a harness comprises a mechanism comprising a pop-lock, a magnet, VELCRO®, locking pins, clips, or a key-in arms mechanism.
34. The method of any of embodiments 31-33, wherein the treatment unit comprises an ultrasound transducer.
35. The method of embodiment 34, wherein the treatment unit comprises a mechanical lens comprising a plurality of concentric rings and configured to adjust ultrasonic waves emitted by the ultrasound transducer.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"). Disease, disorder, and condition are used interchangeably herein.

Embodiments of the present invention include the prophylactic use of the wearable harness before a subject begins to suffer from the specified disease, disorder or condition. As used herein, "prophylactic treatment," "preventive treatment," "prevent," "preventing" or "prevention" contemplates an action that occurs before a subject begins to suffer from the specified disease, disorder or condition. In some embodiments, the terms encompass the inhibition or reduction of the seriousness, progression, or recurrence of a symptom of the particular disease, disorder or condition. As used herein, and unless otherwise specified, a "prophylactically effective amount" is an amount sufficient to prevent a disease, disorder or condition, or one or more symptoms associated with the disease, disorder or condition, or prevent its recurrence. A prophylactically effective amount means an amount which provides a prophylactic benefit in the prevention of the disease, disorder or condition. The term "prophylactically effective amount" can encompass an amount that improves overall prophylaxis or enhances the prophylactic efficacy of another prophylactic agent.

In some variations, a "subject" to which the use of the harnesses described herein and administration are contemplated is a human, who may be a male or female of any age group, e.g., a pediatric subject (e.g., infant, child, adolescent) or adult subject (e.g., young adult, middle-aged adult or senior adult).

As used herein, and unless otherwise specified, a "therapeutically effective amount" is an amount sufficient to provide a therapeutic benefit in the treatment of a disease, disorder or condition, or to delay or minimize one or more symptoms associated with the disease, disorder or condition. A therapeutically effective amount means an amount which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. It is to be appreciated that embodiments of the methods and apparatuses discussed herein are not limited in application to the details of construction and the arrangement of components set forth in the foregoing description or illustrated in the accompanying drawings. The methods and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Accordingly, the foregoing description and drawings are by way of example only, and the scope of the invention should be determined from proper construction of the appended claims, and their equivalents.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

What is claimed is:

1. A system for securing an ultrasound transducer over a spleen of a subject, the system comprising:
- a harness comprising:
  - a front portion configured to hold a power pack and configured to be positioned over the subject's chest;
  - a rear portion configured to be positioned over the subject's back, and connected to the front portion by a first shoulder strap and a second shoulder strap,
    - wherein each shoulder strap comprises shoulder strap scales that extend lengthwise along each shoulder strap for adjustment to a set length every time the harness is worn by the subject,
    - wherein a connection region between the first shoulder strap and the rear portion and a connection region between the second shoulder strap and the rear portion comprise an adjustable clasp,
    - wherein the adjustable clasp is configured to connect and disconnect and adjust a connection position between the rear portion and the first shoulder strap or the rear portion and the second shoulder strap,
    - wherein the connection position comprises an overlap region between the first shoulder strap and the rear portion and the second shoulder strap and the rear portion;
  - an adjustable waist strap configured to wrap around a subject's waist and connect the front portion and the rear portion, wherein the adjustable waist strap comprises a waist strap scale that extends lengthwise along the adjustable waist strap for adjustment to a set length every time the harness is worn by the subject; and
  - a transducer securing portion located on the adjustable waist strap and configured to be positioned over a spleen of a subject,
    - wherein the transducer securing portion comprises a two-dimensional transducer securing portion scale that extends length-wise and height-wise along the exterior of the transducer securing portion,
    - wherein the two-dimensional transducer securing portion scale is benchmarked relative to an anatomical landmark of the subject and is configured to align the ultrasound transducer so that the ultrasound transducer is placed in the same position inside the transducer securing portion every time the harness is worn by the subject; and
- a treatment unit comprising:
  - the ultrasound transducer configured to couple to the transducer securing portion of the harness, wherein the ultrasound transducer is positioned in the same location above the subject's spleen every time the harness is worn.

2. The system of claim 1, wherein the transducer securing portion receives and secures an ultrasound transducer with a mechanism comprising a pop-lock, a magnet, VELCRO®, locking pins, clips, or a key-in arms mechanism.

3. The system of claim 1, further comprising: a mechanical lens positioned between the ultrasound transducer and the subject, wherein the mechanical lens comprising a plurality of concentric rings, and wherein the mechanical lens is configured to adjust ultrasonic waves emitted by the ultrasound transducer to a specific focal distance.

4. The system of claim 3, wherein the focal distance is 0.2-20 cm.

5. A harness for positioning an ultrasound transducer to a subject, the harness comprising:

a front portion configured to hold a power pack and be positioned over the subject's chest;

a rear portion configured to be positioned over the subject's back, and is connected to the front portion by a first shoulder strap and a second shoulder strap, wherein each shoulder strap comprises shoulder strap scales that extend lengthwise along each shoulder strap for adjustment to a set length every time the harness is worn by the subject, wherein a connection region between the first shoulder strap and the rear portion and a connection region between the second shoulder strap and the rear portion comprise an adjustable clasp, wherein the adjustable clasp is configured to connect and disconnect and adjust a connection position between the rear portion and the first shoulder strap or the rear portion and the second shoulder strap, wherein the connection position comprises an overlap region between the first shoulder strap and the rear portion or the second shoulder strap and the rear portion;

an adjustable waist strap configured to wrap around a subject's waist and connect the front portion and the rear portion, wherein the adjustable waist strap comprises a waist strap scale that extends lengthwise along the adjustable waist strap for adjustment to a set length every time the harness is worn by the subject; and a transducer securing portion located on the adjustable waist strap and configured to be positioned over a spleen of a subject, wherein the transducer securing portion comprises a two-dimensional transducer securing portion scale that extends length-wise and height-wise along the exterior of the transducer securing portion, wherein the two-dimensional transducer securing portion scale is benchmarked relative to one or more anatomical landmarks of the subject and is configured to align the ultrasound transducer so that the ultrasound transducer is placed in the same position inside the transducer securing portion every time the harness is worn by the subject.

6. The harness of claim 5, wherein the transducer securing portion is configured to receive a treatment unit such that the harness positions the treatment unit over the spleen of the subject.

7. The harness of claim 6, wherein the treatment unit comprises an ultrasound transducer.

8. The harness of claim 7, wherein the treatment unit further comprises a mechanical lens comprising a plurality of concentric rings and configured to adjust ultrasonic waves emitted by the ultrasound transducer.

9. A system for securing an ultrasound transducer over a spleen of a subject, the system comprising:

a harness of claim 5; and an ultrasound transducer configured to couple to the transducer securing portion of the harness.

10. A method of using a harness of claim 5 for positioning an ultrasound transducer to a subject, the method comprising:

securing a treatment unit to a transducer securing portion of a harness;

placing the harness on a subject such that the treatment unit is positioned over a spleen of the subject.

11. The method of claim 10, wherein securing a treatment unit to a transducer securing portion of a harness comprises positioning the treatment unit to the transducer securing portion with the guidance of a two-dimensional transducer securing portion scale on the transducer securing portion so that the treatment unit is placed in the same position inside the transducer securing portion of the harness every time the harness is worn by the subject.

12. The method of claim 11, wherein securing a treatment unit to a transducer securing portion of a harness comprises a mechanism comprising a pop-lock, a magnet, VELCRO®, locking pins, clips, or a key-in arms mechanism.

13. The method of claim 10, wherein the treatment unit comprises an ultrasound transducer.

14. The method of claim 13, wherein the treatment unit comprises a mechanical lens comprising a plurality of concentric rings and configured to adjust ultrasonic waves emitted by the ultrasound transducer.

* * * * *